United States Patent
Cotti Comettini et al.

(10) Patent No.: US 9,200,302 B2
(45) Date of Patent: Dec. 1, 2015

(54) PROCESS FOR THE RAPID HYDROLYSIS OF HIGH SOLIDS BIOMASS

(75) Inventors: Marco Cotti Comettini, Trivero (IT); Paolo Torre, Arenzano (IT); Francesco Cherchi, Campobasso (IT); Alberto Riva, Arquata Scrivia (IT); Simone Ferrero, Tortona (IT); Piero Ottonello, Genoa (IT); Mirko Garbero, Turin (IT)

(73) Assignee: Beta Renewables S.p.A., Tortona (AL) (IT)

( * ) Notice: Subject to any disclaimer, the term of this patent is extended or adjusted under 35 U.S.C. 154(b) by 1103 days.

(21) Appl. No.: 13/260,281
(22) PCT Filed: Mar. 31, 2010
(86) PCT No.: PCT/IB2010/051413
§ 371 (c)(1), (2), (4) Date: Sep. 24, 2011
(87) PCT Pub. No.: WO2010/113130
PCT Pub. Date: Oct. 7, 2010

(65) Prior Publication Data
US 2012/0055466 A1 Mar. 8, 2012

(30) Foreign Application Priority Data

| Mar. 31, 2009 | (WO) | PCT/IT2009/000124 |
| Mar. 31, 2009 | (WO) | PCT/IT2009/000127 |
| Dec. 14, 2009 | (WO) | PCT/IB2009/055736 |
| Dec. 14, 2009 | (WO) | PCT/IB2009/055737 |

(51) Int. Cl.
C13K 1/02 (2006.01)
C12P 19/02 (2006.01)

(52) U.S. Cl.
CPC . *C12P 19/02* (2013.01); *C13K 1/02* (2013.01); *C12P 2201/00* (2013.01)

(58) Field of Classification Search
None
See application file for complete search history.

(56) References Cited

U.S. PATENT DOCUMENTS

| 4,014,743 A | 3/1977 | Black |
| 4,578,353 A * | 3/1986 | Assarsson et al. ............ 435/161 |

(Continued)

FOREIGN PATENT DOCUMENTS

| FR | 2609046 A | 7/1988 |
| WO | 0238786 A | 5/2002 |
| WO | 2006056838 A | 6/2006 |
| WO | WO 2006086861 A2 * | 8/2006 |
| WO | WO 2007120210 A2 * | 10/2007 |

OTHER PUBLICATIONS

Larsen, Jan et al, The IBUS Process—Lignocellulosic Bioethanol Close to a Commercial Reality, Chemical Engineering and Technology, Apr. 22, 2008, 765-772, vol. 21, No. 5, Weinheim, DE.

(Continued)

*Primary Examiner* — Melvin C Mayes
*Assistant Examiner* — Stefanie Cohen
(74) *Attorney, Agent, or Firm* — Edwin A. Sisson, Attorney at Law, LLC; Jeffrey J. Banyas

(57) ABSTRACT

The process for the hydrolysis of ligno-cellulosic biomass comprises the steps of A) Contacting a ligno-cellulosic feedstock, the feedstock comprised of biomass having a dry content and water with at least a portion of a solvent, the solvent comprised of water soluble hydrolyzed species; wherein at least some of the water soluble hydrolyzed species are the same as the water soluble hydrolyzed species obtainable from the hydrolysis of the biomass in the feedstock;

B) maintaining the contact between the feedstock of the feedstock stream and the solvent at a temperature in the range of 20° C. to 200° C. for a time in the range of 5 minutes to 72 hours to create a hydrolyzed product from the biomass in the feedstock.

11 Claims, 7 Drawing Sheets

(56) References Cited

U.S. PATENT DOCUMENTS

| | | |
|---|---|---|
| 5,733,758 A | 3/1998 | Nguyen |
| 2003/0109011 A1* | 6/2003 | Hood et al. .................. 435/105 |
| 2006/0281157 A1 | 12/2006 | Chotani et al. |
| 2009/0176286 A1* | 7/2009 | O'Connor et al. ............ 435/139 |
| 2011/0094505 A1* | 4/2011 | Bulla et al. ...................... 127/37 |

OTHER PUBLICATIONS

Gibbons, W.R. et al, Fuel Ethanol and High Protein Feed from Corn and Corn Whey Mixtures in a Farm Scale Plant, Biotechnology and Bioengineering, 1983, 2127-2148, vol. 25, No. 9.

International Search Report for PCT/IB/2010/051413, EPO, Nov. 9, 2010.

* cited by examiner

PROCESS FOR THE RAPID HYDROLYSIS OF HIGH SOLIDS BIOMASS

CLAIM OF PRIORITY

This patent application claims priority of patent applications PCT/IT2009/000124 filed on Mar. 31, 2009, PCT/IT2009/000127 filed on Mar. 31, 2009, PCT/IB2009/055736 filed on Dec. 14, 2009, and PCT/IB2009/055737 filed on Dec. 14, 2009.

BACKGROUND

French Patent Application No 2609046 teaches hydrolysis of starch in the presence of starch hyrdrolyzing enzymes. Starch is known to be extracted from food and grain plants. One in the art knows that starch is easily hydrolyzed due to its chemical bonds, whereas cellulose is not easily hydrolyzed. The patent teaches to add water to the ground dry starch to adjust the concentration in ground starchy substratum, expressed in dry matters, to a value understood between 50 and 400 g/liter of the middle of fermentation. The French patent application mentions nothing of applicability to cellulosic feedstocks.

It is known in the art that the energy cost of distillation of ethanol from a fermentation process is dramatically reduced if the fermentation broth contains more than 4% ethanol. This requires a sugar concentration above 8% (w/w), which with most types of biomass, in particular lignocellulosic biomasses, corresponds to an initial dry matter content above 20%.

It is therefore critical to be able to utilize lignocellulosic-containing biomasses with high dry matter contents, preferably above 20% by weight.

Enzymatic hydrolysis of biomass has previously been described. However, in the case of lignocellulosic biomasses, only material consisting in fibers and particles with an average size below 1inch (25.4 mm) and furthermore having a relatively low dry matter content, i.e. below 20% (w/w), have successfully been hydrolyzed.

Enzymatic hydrolysis of biomass has traditionally been carried out in stirred tank reactors equipped with impellers (e.g. Rushton turbine or Intemig impeller) mounted on a centrally placed impeller shaft similar to what is used in the fermentation industry. Due to this equipment, high viscosity solutions, very sticky or very dry material cannot be stirred efficiently and will result inhomogeneous, maintaining areas with very poor or no mixing. Furthermore, stirring of such solutions requires very large energy inputs, which are detrimental to the economy of the process. Operating with polysaccharide-containing biomasses has therefore previously restricted the upper possible limit to app. 20% (w/w).

This is evidenced in U.S. Pat. No. 4,409,329 which describes hydrolysis of solid cellulose material to sugar, where cellulose is hydrolyzed to simple sugars by treating a granular slurry of 3-20% (w/w) solid feed containing 30-80% (w/w) cellulose, with a cellulase enzyme complex. The solid cellulose-containing charge had a mean particle size ranging from 0.01 to 1 inch (0.0254-25.4 mm) in diameter. Perforated rotor blades were used for mixing. The teaching of the patent is to utilize a very high shear rate, on the order of 50,000 to 200,000 feet/minute/foot throughout the reaction zone.

US2002117167A describes enzymatic hydrolysis of hemicellulose in biomass material, comprising solubilizing at least a portion of hemicellulose and hydrolyzing the solubilized hemicellulose to produce at least one monosaccharide. The selected biomass is preferably an aqueous slurry of raw or pre-treated material. The biomass material may be any cellulosic material that includes hemicellulose. The process is described as being especially effective with grain fibers such as corn, wheat, rice, oats or barley. However, as noted in the examples, the cellulose is not hydrolyzed.

US2004005674A describes a process for enzymatic hydrolysis of lignocellulose. Degradation of lignocellulose to sugars comprises contacting the lignocellulose with at least one auxiliary enzyme and at least one cellulase. The lignocellulosic material was ground (the average fiber size of the material was not further specified) and had a low dry matter content (0.2 g of ground stover material in 10 ml of enzyme solution).

WO 2006/056838 describes a process for liquefaction and saccharification of polysaccharide-containing biomasses, having a relatively high dry matter content. It combines enzymatic hydrolysis with a type of mixing relying on the principle of gravity, ensuring that the biomasses are subjected to mechanical forces, primarily shear and tear forces.

The above processes are expensive to operate due to their high shear requirements and time to hydrolyze the feedstock. There exists therefore a need to use economical designs while at the same time treating high dry content biomass.

SUMMARY

It is well known in the art that cellulose is very difficult to break down into sugar. Efforts to hydrolyze the cellulosic biomasses have generally proved uneconomical. While the cellulosic containing biomass streams can be treated to increase the accessibility of the cellulose to hydrolysis catalysts, such as enzymes, it is still very difficult in time and energy to convert the cellulose to its basic sugars. It is for this reason, that prior art systems remove the cellulosic components first and hydrolyze the starch or free sugar component alone. These systems are referred to as first generation processes. The difficulty of the cellulosic hydrolysis is evidenced in the recent prior art patents cited in the background section which subject the cellulosic materials to high shear and long times to break the fibers.

This specification discloses a hydrolysis process which does not need shear and hydrolyze the cellulose in a very short time.

This specification therefore discloses a process for the hydrolysis of high dry content biomass comprising the steps of contacting a feedstock comprised of biomass having both dry content and water with at least a portion of a solvent comprised of water soluble hydrolyzed species; wherein at least some of the water soluble hydrolyzed species are the same as the water soluble hydrolyzed species obtainable from the hydrolysis of the biomass, maintaining the contact between the feedstock and the solvent in the presence of a catalyst composition at a temperature in the range of 20° C. to 95° C. for a time in the range of 5 minutes to 72 hours to create a hydrolyzed product from the biomass.

This specification discloses that the process for the hydrolysis of biomass can also comprise the steps of A) Apportioning an amount of biomass having a dry content and water into at least a first feedstock stream and a second feedstock stream, B) Creating a first solvent stream by hydrolyzing the first feedstock stream with the addition of a catalyst to the first feedstock stream wherein the catalyst amount is in range of 0.1 to 150 FPU/g of dry content in all the feedstock streams and conducting the hydrolysis at a temperature in the range of 20° C. to 95° C. for a time in the range of 5 minutes to 8 hours, C) Contacting at least one of the feedstock streams which is not the first feedstock stream with the first solvent stream and D) maintaining the contact between the at least one feedstock which is not the first feedstock stream and the first solvent stream at a temperature in the range of 20° C. to 95° C. for a time in the range of 5 minutes to 72 hours to create a hydrolyzed product from the biomass.

It is further disclosed that at least a portion of the catalyst composition be contacted with the feedstock prior to, immediately at, or after contacting the feedstock with the solvent. It is further disclosed that the ratio of the biomass to water of the feedstock can be greater than 1:6, or greater than 1:5, or greater than 1:4, or greater than 1:3, or greater than 1:2.5, or greater than 1:2, or greater than 1:1.5 or greater than 1:1 or greater than 1:0.9.

It is further disclosed that the amount of biomass to water in the feedstock be in the ratio ranges of 1:4 to 9:1; 1.3.9 to 9:1, 1:3.5 to 9:1, 1:3.25 to 9:1, 1:3 to 9:1, 1:2.9 to 9:1, 1:2 to 9:1, 1.15 to 9:1, 1:1 to 9:1, and 1:0.9 to 9:1.

It is further disclosed that the ratio of the weight of the solvent contacted with the feed stock to the weight of the feedstock at the moment of contact can be in any one of the ranges of 1:99 to 99:1, 10:90 to 90:10, 20:80 to 90:10, 30:70 to 90:10, 40:60 to 90:10, 50:50 to 90:10, and 60:40 to 90:10.

It is further disclosed that the catalyst comprises an enzyme and the enzyme is capable of converting a compound in the biomass to a sugar or low molecular weight sugar polymer.

It is further disclosed that the enzyme be capable of hydrolyzing cellulose, preferably to glucose.

It is further disclosed that the process could be a batch process wherein the catalyst composition is introduced into the vessel before, simultaneously with, or after introduction of the feedstock and the feedstock and the solvent are maintained in the vessel in the temperature range for the amount of time, and after maintaining the feedstock, the solvent and catalyst in the vessel in the temperature range for the amount of time, a weight of the hydrolyzed product is removed from the vessel, wherein the weight of the hydrolyzed product removed is substantially equivalent to the weight of the feedstock plus the catalyst composition introduced plus the weight of all the other materials other than the solvent introduced into the vessel. The process could also contain a second solvent stream from a previously hydrolyzed batch. The removal of the product could be complete or a portion of the product remain in the vessel.

It is further disclosed that the process could be a continuous process wherein the feedstock of the at least one feedstock stream which is not the first feedstock stream and the solvent of the first solvent stream are continuously introduced into a vessel already containing the solvent stream, the catalyst composition is continuously introduced into the vessel, and the hydrolyzed product is continuously removed from the vessel, wherein the weight of the hydrolyzed product removed during a specified amount of time is equivalent to the weight of feedstock plus the catalyst composition plus the weight of all the other materials other than the solvent introduced into the vessel during the specified amount of time.

It is further disclosed that the processes could have a premixing step based upon a recycle loop of the product solvent stream wherein a portion of the solvent is mixed with at least a portion of the feedstock prior to introduction to the vessel and all ratios of the solvent to the feedstock are based upon the total amount of solvent which is the amount of solvent in the vessel plus the amount of any solvent mixed with the at least a portion of the feedstock stream.

It is further disclosed that the solids be separated from the hydrolyzed stream and the solids optionally recycled into the hydrolysis vessel. It is disclosed that the solids may also be purged prior to adding to the hydrolysis vessel or not added to the hydrolysis vessel at all.

DETAILED DESCRIPTION

Figure 1:
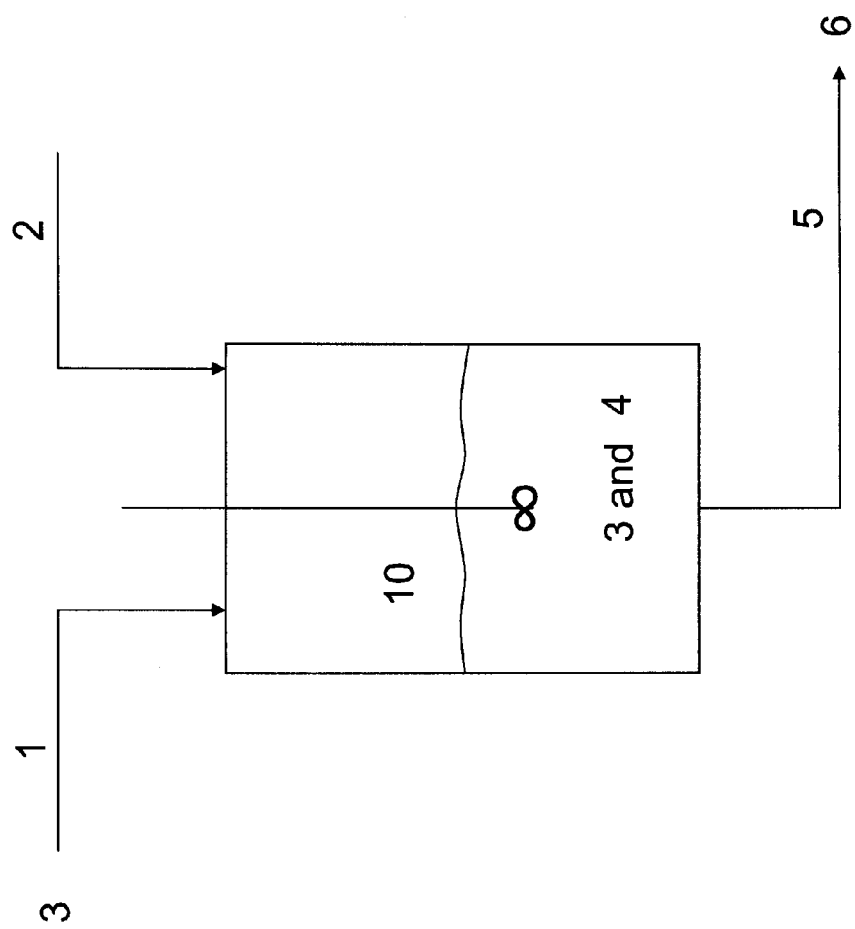
FIG. 1 is a schematic of a continuous hydrolysis process.

This process utilizes the discovery that the enzymatic hydrolysis of cellulose can occur very rapidly and thus optionally avoiding shear and excess water when the hydrolysis is done in the presence of a substantial amount of already hydrolyzed products from the biomass. In so doing, the practioner may avoid the use of special mixers and the high costs of mixing described in the prior art proposals.

The process begins with the selection of a feedstock. The feedstock is comprised of biomass having a dry content and water. Usually the water is not free water, but is water absorbed into the biomass itself. This biomass is often expressed according to its dry content (non-water). A 20% dry content biomass corresponds to a biomass that has 80% water and 20% non-water, or otherwise solid content. The term biomass and water is the dry content of the biomass plus the absorbed and free water and water which may have been added. For example, the amount of biomass plus water for 100 kg of biomass with 20% dry content is 100 kg. The amount of biomass plus water for 100 kg of biomass with 20% dry content plus 10 kg of water is 110 kg.

The process described is believed capable of utilizing a feedstock of biomass and water where the dry matter content to water of the feedstock is preferably 15 to 80%, 20 to 80%, or 21 to 80%, preferably 25 to 70%, or 26-70%, more preferably 25 to 60%, or 26 to 60%, even more preferably 25 to 50%, or 26 to 50% or 25 to 40%, or 26% to 40% and most preferably 25 to 35%, or 26 to 35%, or 26 to 34%, or 31% to 49%.

This can alternatively be expressed as a minimum dry content, i.e. as a weight percent of the dry content relative to the water in the feedstock. This would correspond to at least 18 weight percent dry content, preferably to at least 21 or 20 weight percent dry content, preferably at least 25 weight percent dry content, more preferably at least 30 weight percent dry content, and most preferably at least 40 weight percent dry content. The upper limit of these contents is by definition 100%, but in practice 80 weight percent would be the upper limit to these contents if they were expressed in ranges.

The process described herein is believed capable of handling an almost 100% dry content. Recognizing of course, that some water is essential for the hydrolysis reaction.

Therefore, ranges suitable for this invention are biomasses having dry contents of greater than 18%, 20%, 21%, 25%, 26%, 30%, 31%, 35%, 36%, 40%, 50%, 60% and 80% with a upper limit of 80%, 90%, for each lower limit.

The preferred distribution of fiber and particle sizes of the biomass may involve the ranges of 0-150 mm, preferably, 5-125 mm, more preferably, 10-100 mm, even more preferably 15-30 to 90 mm or 20-80 mm and most preferably 26 to 70 mm.

The preferred distribution of fiber and particle sizes is defined as at least 20% (w/w) of the biomass ranging within the preferred interval.

An advantage of this process is that it can be conducted without adding an inorganic acid preferably selected from the group consisting of sulfuric acid, hydrochloric acid, phosphoric acid, and the like, or mixtures thereof or without lignin solubilizing organic solvents such as those selected from the group consisting of carbon, cetones and acetones of 2 to 6 carbon atoms and mixtures thereof, methanol, ethanol.

Another advantage is that this reaction can be done at atmospheric pressure. Alternatively, it is believed that the temperature can be raised so that the reaction can be done with or without enzymes at pressures associated with the temperature in the range of 100° C. to 200° C.

Plant biomass is a preferred feedstock. Apart from starch the three major constituents in plant biomass are cellulose, hemicellulose and lignin, which are commonly referred to by the generic term lignocellulose. Polysaccharide-containing biomass is a generic term that includes both starch and ligno-cellulosic biomasses. Therefore, some types of feedstocks can be plant biomass, polysaccharide containing biomass, and lignocellulosic biomass. To be clear, in this specification, a ligno-cellulosic biomass may or may not contain starch.

This process is primarily aimed at second generation hydrolysis production where the ligno-cellulosic feedstock contains greater than 5% by weight of the dry content of cellulose. While 5% by weight of the dry content is a preferred amount, an even more preferred amount is a cellulose content greater than 10% by weight of the dry content of the feedstock, with greater than at least 15% by weight of the dry content of the feedstock being most preferred.

While the feedstock can be free of starch, substantially free of starch, or have a starch content of 0. Starch, if present, can be less than 75% by weight of the dry content. There is no preferred starch range as its presence is not believed to affect the hydrolysis of the cellulose. Ranges for the starch amount, if present, are between 0 and 75% by weight of the dry content, 0 to 50% by weight of the dry content, 0 to 30% by weight of the dry content and 0 to 25% by weight of the dry content.

A pre-treatment is often used to ensure that the structure of the lignocellulosic content is rendered more accessible to the catalysts, such as enzymes, and at the same time the concentrations of harmful inhibitory by-products such as acetic acid, furfural and hydroxymethyl furfural remain substantially low.

There are several strategies to achieve increased accessibility, many of which may yet be invented. The current strategies imply subjecting the lignocellulosic material to temperatures between 110-250° C. for 1-60 min e.g.:

Hot Water Extraction
Multistage dilute acid hydrolysis, which removes dissolved material before inhibitory substances are formed
  Dilute acid hydrolyses at relatively low severity conditions
  Alkaline wet oxidation
  Steam explosion
  Almost any pre-treatment with subsequent detoxification If a hydrothermal pre-treatment is chosen, the following conditions are preferred:

Pre-treatment temperature: 110-250° C., preferably 120-240° C., more preferably 130-230° C., more preferably 140-220° C., more preferably 150-210° C., more preferably 160-200° C., even more preferably 170-200° C. or most preferably 180-200° C.

Pre-treatment time: 1-60 min, preferably 2-55 min, more preferably 3-50 min, more preferably 4-45 min, more preferably 5-40 min, more preferably 5-35 min, more preferably 5-30 min, more preferably 5-25 min, more preferably 5-20 min and most preferably 5-15 min.

Dry matter content after pre-treatment is preferably at least 20% (w/w). Other preferable higher limits are contemplated below.

Polysaccharide-containing biomasses according to the present invention include any material containing polymeric sugars e.g. in the form of starch as well as refined starch, cellulose and hemicellulose. However, as discussed earlier, the starch is not a primary component.

Relevant types of biomasses for hydrolysis and mixing according to the present invention may include biomasses derived from agricultural crops such as e.g.: containing grains; corn stover, bagasse, straw e.g. from rice, wheat, rye, oat, barley, rape, sorghum; tubers e.g. beet, potato.

The ligno-cellulosic biomass feedstock is preferably from the family usually called grasses.

The proper name is the family known as Poaceae or Gramineae in the Class Liliopsida (the monocots) of the flowering plants. Plants of this family are usually called grasses, and include bamboo. There are about 600 genera and some 9,000-10,000 or more species of grasses (Kew Index of World Grass Species).

Poaceae includes the staple food grains and cereal crops grown around the world, lawn and forage grasses, and bamboo. Poaceae generally have hollow stems called culms, which are plugged (solid) at intervals called nodes, the points along the culm at which leaves arise. Grass Leaves are usually alternate, distichous (in one plane) or rarely spiral, and parallel-veined. Each leaf is differentiated into a lower sheath which hugs the stem for a distance and a blade with margins usually entire. The leaf blades of many grasses are hardened with silica phytoliths, which helps discourage grazing animals. In some grasses (such as sword grass) this makes the edges of the grass blades sharp enough to cut human skin. A membranous appendage or fringe of hairs, called the ligule, lies at the junction between sheath and blade, preventing water or insects from penetrating into the sheath.

Grass blades grow at the base of the blade and not from elongated stem tips. This low growth point evolved in response to grazing animals and allows grasses to be grazed or mown regularly without severe damage to the plant.

Flowers of Poaceae are characteristically arranged in spikelets, each spikelet having one or more florets (the spikelets are further grouped into panicles or spikes). A spikelet consists of two (or sometimes fewer) bracts at the base, called glumes, followed by one or more florets. A floret consists of the flower surrounded by two bracts called the lemma (the external one) and the palea (the internal). The flowers are usually hermaphroditic (maize, monoecious, is an exception) and pollination is almost always anemophilous. The perianth is reduced to two scales, called lodicules, that expand and contract to spread the lemma and palea; these are generally interpreted to be modified sepals. This complex structure can be seen in the image on the left, portraying a wheat (*Triticum aestivum*) spike.

The fruit of Poaceae is a caryopsis in which the seed coat is fused to the fruit wall and thus, not separable from it (as in a maize kernel).

There are three general classifications of growth habit present in grasses; bunch-type (also called caespitose), stoloniferous and rhizomatous.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized Kranz leaf anatomy that particularly adapts them to hot climates and an atmosphere low in carbon dioxide.

C3 grasses are referred to as "cool season grasses" while C4 plants are considered "warm season grasses". Grasses may be either annual or perennial. Examples of annual cool season are wheat, rye, annual bluegrass (annual meadowgrass, *Poa annua* and oat). Examples of perennial cool season are orchardgrass (cocksfoot, *Dactylis glomerata*), fescue (*Festuca* spp), Kentucky Bluegrass and perennial ryegrass (*Lolium perenne*). Examples of annual warm season are corn, sudangrass and pearl millet. Examples of Perennial Warm Season are big bluestem, indiangrass, bermudagrass and switchgrass.

One classification of the grass family recognizes twelve subfamilies: These are 1) anomochlooideae, a small lineage of broad-leaved grasses that includes two genera (*Anomochloa, Streptochaeta*); 2) Pharoideae, a small lineage of grasses that includes three genera, including *Pharus* and *Leptaspis;* 3) Puelioideae a small lineage that includes the African genus *Puelia;* 4) Pooideae which includes wheat, barely, oats, brome-grass (Bronnus) and reed-grasses (*Calamagrostis*); 5) Bambusoideae which includes bamboo; 6) Ehrhartoideae, which includes rice, and wild rice; 7) Arundinoideae, which includes the giant reed and common reed 8) Centothecoideae, a small subfamily of 11 genera that is sometimes included in Panicoideae; 9) Chloridoideae including the lovegrasses (*Eragrostis*, ca. 350 species, including teff), dropseeds (*Sporobolus*, some 160 species), finger millet (*Eleusine coracana* (L.) Gaertn.), and the mushy grasses (*Muhlenbergia*, ca. 175 species); 10) Panicoideae including panic grass, maize, sorghum, sugar cane, most millets, fonio and bluestem grasses. 11) Micrairoideae; 12) Danthoniodieae including pampas grass; with Poa which is a genus of about 500 species of grasses, native to the temperate regions of both hemispheres.

Agricultural grasses grown for their edible seeds are called cereals. Three common cereals are rice, wheat and maize (corn). Of all crops, 70% are grasses.

Sugarcane is the major source of sugar production. Grasses are used for construction. Scaffolding made from bamboo is able to withstand typhoon force winds that would break steel scaffolding. Larger bamboos and *Arundo donax* have stout culms that can be used in a manner similar to timber, and grass roots stabilize the sod of sod houses. *Arundo* is used to make reeds for woodwind instruments, and bamboo is used for innumerable implements.

Therefore a preferred lignocellulosic biomass is selected from the group consisting of the grasses. Alternatively phrased, the preferred lignocellulosic biomass is selected from the group consisting of the plants belonging to the Poaceae or Gramineae family. In most instant the starch will not have been extracted. Thus another preferred lignocellulosic biomass is one selected from the group consisting of the grasses which have not had the starch extracted. Alternatively phrased, the preferred lignocellulosic biomass is selected from the group consisting of the plants belonging to the Poaceae or Gramineae family which has not its starch extracted. Extracted is different from removed. The corn plant has the ear and the stover. Removal of the ear removes the primary starch component but is not extracting the starch. Extracting the starch is separating the starch from the cellulosic starch composition through a chemical or physical process other than cutting or chopping.

The lignocellulosic biomass may be cut into pieces where 20% (w/w) of the biomass preferably ranges within 26-70 mm, before pre-treatment. The pre-treated material has preferably a dry matter content above 20% before entering the process. Besides liberating the carbohydrates from the biomass, the pre-treatment process sterilizes and partly dissolves the biomass and at the same time washes out potassium chloride from the lignin fraction.

The biomass will contain some compounds which are hydrolysable into a water-soluble species obtainable from the hydrolysis of the biomass. In the case of water soluble hydrolyzed species of cellulose, cellulose can be hydrolyzed into glucose, cellobiose, and higher glucose polymers and includes dimers and oligomers. Thus some of the water soluble hydrolyzed species of cellulose are glucose, cellobiose, and higher glucose polymers and includes their respective dimers and oligomers. Cellulose is hydrolysed into glucose by the carbohydrolytic cellulases. Thus the carbohydrolytic cellulases are examples of catalysts for the hydrolysis of cellulose.

The prevalent understanding of the cellulolytic system divides the cellulases into three classes; exo-1,4-β-D-glucanases or cellobiohydrolases (CBH) (EC 3.2.1.91), which cleave off cellobiose units from the ends of cellulose chains; endo-1,4-β-D-glucanases (EG) (EC 3.2.1.4), which hydrolyse internal β-1,4-glucosidic bonds randomly in the cellulose chain; 1,4-β-D-glucosidase (EC 3.2.1.21), which hydrolyses cellobiose to glucose and also cleaves off glucose units from cellooligosaccharides. Therefore, if the biomass contains cellulose, then glucose is a water soluble hydrolyzed species obtainable from the hydrolysis of the biomass and the afore mentioned cellulases are specific examples, as well as those mentioned in the experimental section, of catalysts for the hydrolysis of cellulose.

By similar analysis, the hydrolysis products of hemicellulose are water soluble species obtainable from the hydrolysis of the biomass, assuming of course, that the biomass contains hemicellulose. Hemicellulose includes xylan, glucuronoxylan, arabinoxylan, glucomannan, and xyloglucan. The different sugars in hemicellulose are liberated by the hemicellulases. The hemicellulytic system is more complex than the cellulolytic system due to the heterologous nature of hemicellulose. The systems may involve among others, endo-1,4-β-D-xylanases (EC 3.2.1.8), which hydrolyse internal bonds in the xylan chain; 1,4-β-D-xylosidases (EC 3.2.1.37), which attack xylooligosaccharides from the non-reducing end and liberate xylose; endo-1,4-β-D-mannanases (EC 3.2.1.78), which cleave internal bonds; 1,4-β-D-mannosidases (EC 3.2.1.25), which cleave mannooligosaccharides to mannose. The side groups are removed by a number of enzymes; such as α-D-galactosidases (EC 3.2.1.22), α-L-arabinofuranosidases (EC 3.2.1.55), α-D-glucuronidases (EC 3.2.1.139), cinnamoyl esterases (EC 3.1.1.-), acetyl xylan esterases (EC 3.1.1.6) and feruloyl esterases (EC 3.1.1.73). Therefore, if the biomass contains hemicellulose, then xylose and mannose are examples of a water soluble hydrolyzed species obtainable from the hydrolysis of the hemicellulose containing biomass and the afore mentioned hemicellulases are specific examples, as well as those mentioned in the experimental section, of catalysts for the hydrolysis of hemicellulose.

Included in the process is a catalyst composition. The catalyst composition consists of the catalyst, the carrier, and other additives/ingredients used to introduce the catalyst to the process. As discussed above, the catalyst may comprise at least one enzyme or microorganism which converts at least one of the compounds in the biomass to a compound or compounds of lower molecular weight, down to, and including, the basic sugar or carbohydrate used to make the compound in the biomass. The enzymes capable of doing this for the various polysaccharides such as cellulose, hemicellulose, and starch are well known in the art and would include those not invented yet.

The catalyst composition may also comprise an inorganic acid preferably selected from the group consisting of sulfuric acid, hydrochloric acid, phosphoric acid, and the like, or mixtures thereof. The inorganic acid is believed useful for processing at temperatures greater than 100° C. The process may also be run specifically without the addition of an inorganic acid.

It is typical to add the catalyst to the process with a carrier, such as water or an organic based material. For mass balance purposes, the term catalyst composition therefore includes the catalyst(s) plus the carrier(s) used to add the catalyst(s) to the process. If a pH buffer is added with the catalyst, then it is part of the catalyst composition as well.

Often the ligno-cellulosic biomass will contain starch. The more important enzymes for use in starch hydrolysis are alpha-amylases (1,4-α-D-glucan glucanohydrolases, (EC 3.2.1.1)). These are endo-acting hydrolases which cleave 1,4-α-D-glucosidic bonds and can bypass but cannot hydrolyse 1,6-α-D-glucosidic branchpoints. However, also exo-acting glycoamylases such as beta-amylase (EC 3.2.1.2) and pullulanase (EC 3.2.1.41) can be used for starch hydrolysis. The result of starch hydrolysis is primarily glucose, maltose, maltotriose, α-dextrin and varying amounts of oligosaccharides. When the starch-based hydrolysate is used for fermentation it can be advantageous to add proteolytic enzymes. Such enzymes may prevent flocculation of the microorganism and may generate amino acids available to the microorganism. Therefore, if the biomass contains starch, then glucose, maltose, maltotriose, α-dextrin and oligosaccharides are examples of a water soluble hydrolyzed species obtainable from the hydrolysis of the starch containing biomass and the afore mentioned alpha-amylases are specific examples, as well as those mentioned in the experimental section, of catalysts for the hydrolysis of starch.

While the hydrolysis can utilize the solvent contact processes embodied in FIGS. 1-4, a preferred embodiment with improved efficiency and rate of hydrolysis can be substantially improved by using fresh catalysts. It is believed that over time, a portion of the catalyst in the catalyst composition in embodiments 1, 2, 3 and 4 will degrade over time.

Figure 4:
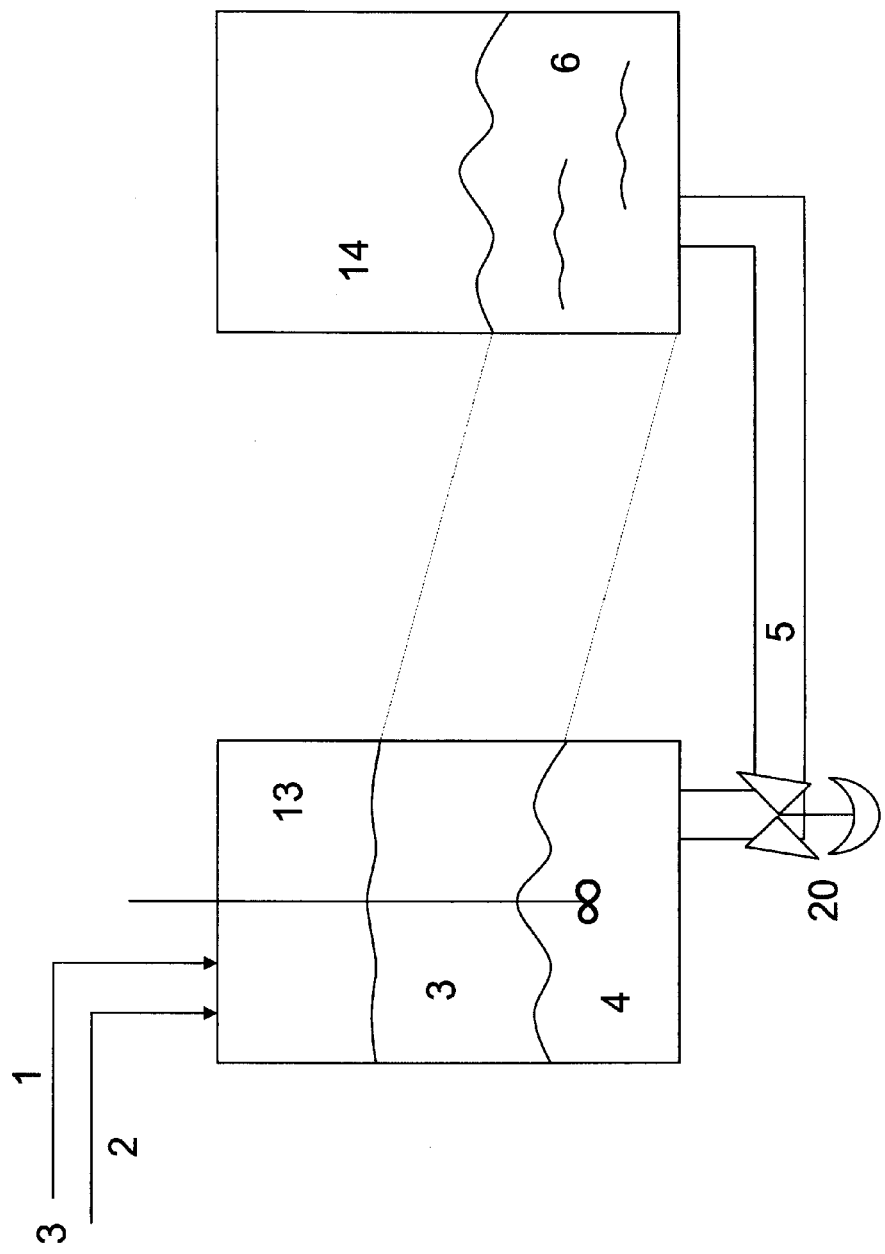
FIG. 4 is a schematic of a batch hydrolysis process.
Figure 5:
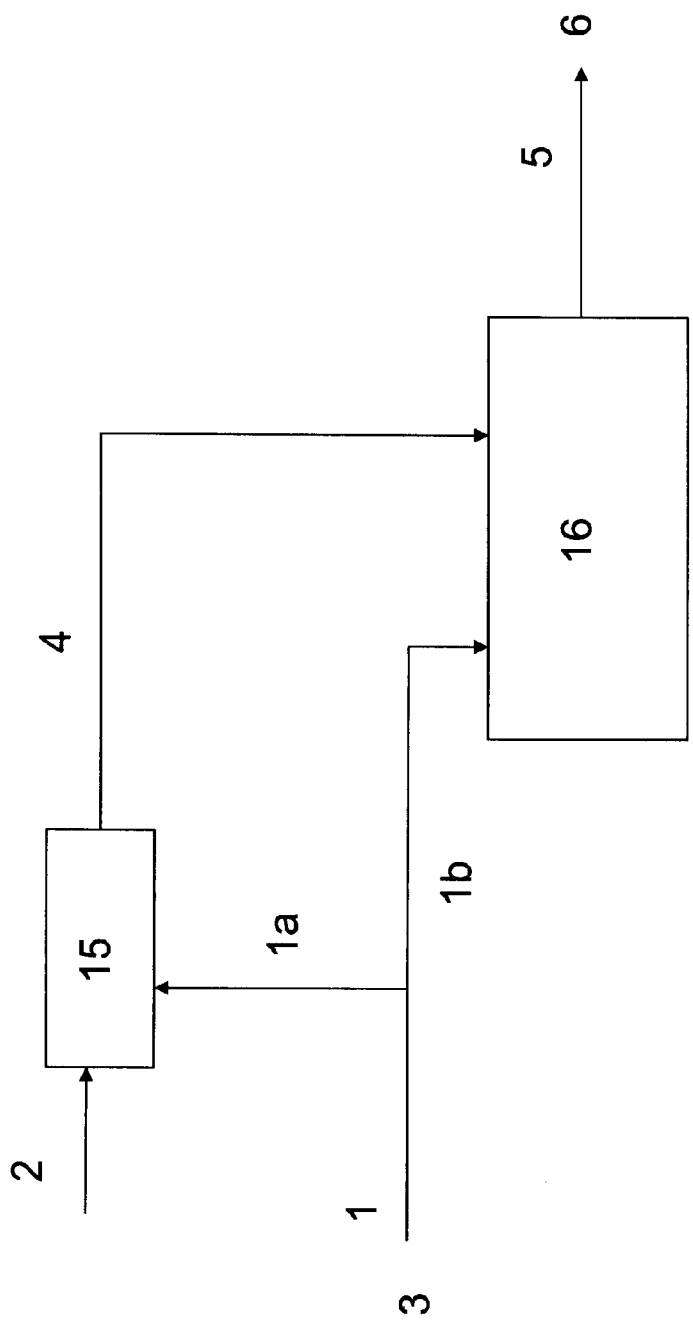
FIG. 5 is a schematic of one embodiment of the improved process showing treatment with excess catalyst.

The process proposed in FIG. 5 splits, or apportions the biomass 3, stream 1 into a least two streams, with the first feedstock stream 1*a* being hydrolyzed in vessel 15 with an excess amount of catalyst introduced in a catalyst composition through stream 2, optionally without the use of the solvent process. After hydrolyzing the first feedstock stream 1 *a* in the presence of excess catalyst in stream 2, the hydrolyzed product 4 is removed from vessel 15 and known as the solvent of the first solvent stream. The first solvent stream 4 is then combined with at least a portion of the remaining feedstock of feedstock stream 1*b* and the solvent hydrolysis process begins in vessel 16. Vessel 16 could correspond to any of vessels 10 in FIG. 1, Vessel 10 or 11 in FIG. 2, Vessel 12 in FIG. 3 and Vessel 13 in FIG. 4. The hydrolyzate product 6 is removed from the vessel as stream 5.

The amount of catalyst needed to treat the first feedstock stream depends greatly upon the type of biomass in the feedstock and the catalyst or enzyme(s) chosen. Therefore, the best expression of the amount of catalyst is based upon the amount required to hydrolyze 100% of the hydrolysable components in a given weight of biomass.

The amount of catalyst needed for the first feedstock stream is in the range of the minimum amount of catalyst required to hydrolyze 100% of the first feedstock stream to twice the amount required to hydrolyze 100% of all the feedstock streams.

This can also be expressed in Filter Paper Units (FPU)/g Dry Matter (DM). FPU is measured and defined according to the NREL Laboratory Analytical Procedure (*Technical Report* NREL/TP-510-42628, January 2008). This method uses the industry standard and measures the cellulose activity in terms of "filter paper units" (FPU) per milliliter of original (undiluted) enzyme solution. For quantitative results the enzyme preparations must be compared on the basis of significant and equal conversion. One filter paper unit for a given enzyme is the amount of enzyme needed to release 2.0 mg of reducing sugar as glucose from 50 mg of filter paper from a Whatman No. 1 filter strip (4% conversion) in 60 minutes at 50° C. and has been designated as the intercept for calculating filter paper cellulose units (FPU) by International Union of Pure and Applied Chemistry (IUPAC) guidelines. Catalytic activity for any of the processes could be in principle supplied in any conceivable form including the addition of microorganisms giving rise to enzymatic activity corresponding to 0.001-150 FPU/g dry matter, preferably 0.001-25 FPU/g dry matter, preferably 0.01-20 FPU/g dry matter, more preferably 0.2-16 FPU/g dry matter, more preferably 2-30 FPU/g dry matter and most preferably between 4 and 25 FPU/g dry matter.

In the hydrolysis step of FIG. 5 (vessel 15), the amount of catalyst or enzyme added to the first feedstock stream is in the ranges of 0.001-150 FPU/g dry matter of all the feedstock streams, preferably 0.001-15 FPU/g dry matter of all the feedstock streams, preferably 0.01-30 FPU/g dry matter of all the feedstock streams, more preferably 0.1-30 FPU/g dry matter of all the feedstock streams, more preferably 1-25 FPU/g dry matter of all the feedstock streams and most preferably less than 20 FPU/g dry matter of all the feedstock streams but greater than 0.1 FPU/g dry matter of all the feedstock streams. While the analysis of FPU is well known, in this instance one would divide the amount of catalyst by the amount of total feedstock and then determine whether that concentration had the FPU within the range. Alternatively, if one knows the FPU of the catalyst concentration, one would add enough catalyst to achieve the required FPU for the given amount of feedstock. After hydrolyzing the first feedstock stream with the catalyst, the hydrolyzed material becomes known as the first solvent stream. The second solvent stream would be liquefied hydrolyzed material of all the feedstock streams and would include the first solvent stream plus the hydrolyzed materials which are not the first feedstock stream. The term all solvent streams would include all the liquified streams used as a solvent and which come in contact with the unreacted biomass.

The first solvent stream as described below can then be used as a solvent for the hydrolysis of the remaining feedstock streams. The remaining feedstock streams can then be introduced into the hydrolysis vessel before, after, or coincident with the introduction of the first solvent stream into the vessel. Processes 1, 2, 3 and 4 are just some types of the processes that could be used to hydrolyze the remaining feedstock streams (those streams which are not the first feedstock stream).

Because the first solvent stream has catalyst that has only been used once and in excess, it is believed to better hydrolyze the remaining streams, because the remaining feedstock streams are subsequently contacted with fresher catalyst than would be used in processes shown in FIGS. 1 through 4 without the pre step of process shown in FIG. 5.

As shown in Experiment No. 5, the feedstock was divided into two portions, with the first portion being treated with the amount of catalyst that would be used were the two portions to be treated together.

For all processes it is also common to control the pH at the optimum conditions for the enzymatic catalytic activity in the range of 3-12, such as 5-10, such as 6-9, such as 7-8 and preferably 4-11.

Due to the high dry content, a special reactor may be needed for the hydrolysis in vessel 15. A reactor believed suitable can be found in WO 2006/056838 and is the object of the invention of that disclosure.

The process also uses a solvent from a solvent stream. In simple terms the composition of the solvent, excluding the water insoluble materials, is what will be similar, if not exactly, the composition product after hydrolysis of the biomass. In most instances solvent will comprise the hydrolyzate obtained from biomass feedstock after hydrolysis and includes the enzymes, buffers, and anything else added to the hydrolysis reaction.

While the solvent is hydrolyzed biomass, the solvent is added to the feedstock, it is not created by the feedstock. For example, in FIG. 4, the batch process, the amount of solvent type material will increase with time as the feedstock is hydrolyzed, although this joins the solvent in the solvent, it is not considered part of the solvent for the purposes of calculating the ratios of solvent to feedstock, which in the case of FIG. 4, is calculated when the feedstock enters the vessel and contacts the solvent.

In practice, the solvent for the solvent stream will generally come from the previously hydrolyzed biomass. If one, for example, separates the hydrolyzate from the enzymes, buffers, insolubles, etc, then the hydrolyzate is the solvent. The solvent stream should comprise water soluble hydrolyzed species, wherein at least some of the water soluble hydrolyzed species are the same as the water soluble hydrolyzed species obtainable or that could be obtained, from the hydrolysis of the biomass feedstock. For example, a preferred mode of operating the batch process of FIG. 4 is to keep a portion of the batch in the vessel to use as the solvent for the following charge. In the continuous process, such as a continuous stirred reactor (CSTR), the solvent is constantly available.

It is well known that in the continuous reactor, the feedstock and catalyst are continuously introduced into the vessel and the product continuously removed. However, the continuously does not always mean without starts and stops, a constant drip for instance is considered a continuous feed yet it is not an exact continuous feed as there are moments when the feed is not continuous. Therefore in the context of the continuous reactor, the phrase continuous means that the feed and products can be each intermittently introduced or withdrawn over time and do not have to be fed and withdrawn at the same time.

As described in the experimental section, when the high dry content biomass is placed into a portion of the solvent, the dissolution and hydrolysis are extremely fast, in fact, visually evident.

The solvent stream, and solvent, therefore includes the water and the water soluble hydrolyzed species. At least some, if not all of the water soluble hydrolyzed species, are the same as the water soluble hydrolyzed species that are obtainable from the hydrolysis of the biomass in the feedstock composition. Because the solvent contains undissolved species, which can be called dispersed solids, for mass balance purposes, unless an item is specifically excluded, the term solvent and solvent stream refer to the total amount of material, in both composition and weight, and includes the water soluble species and water insoluble species, catalyst, carriers, pH buffers, pH control compounds such as acids or bases added during the reaction and other compounds that are present in the solvent.

The process includes a moment of contact, defined as when the feedstock and the solvent are brought together. In the batch process as shown in FIG. 4, this moment of contact occurs when feedstock stream 3, enters the vessel 13 through line 1, and contacts the solvent stream 4 in the bottom of the vessel.

The point of addition of the catalyst composition relative to the contact is not so critical. It can be added to the feedstock stream before the moment of contact of the feedstock with the solvent. It can be added simultaneously at the moment of contact of the feedstock with the solvent, or it can be added after the moment of contact of the feedstock with the solvent. It can also be added to the solvent stream prior to adding the feedstock stream to the solvent stream. It can also be apportioned and added during any combination of the three stages relative to the moment of contact.

The amount of catalyst to be added is easily established from the art and is added on the basis of amount of catalyst per amount of dry content in the biomass, which depends upon the composition of the biomass.

According to the process, the feedstock, the solvent and the catalyst composition and other materials such as a pH buffer and acids/bases used to control the pH through the reaction is preferably be maintained at a temperature within the range of 20° C. to 100° C. and more preferably in the range of 20° C. and 99° C., with 20° C. to 95° C. being the most preferred. This temperature is based upon the best temperature for the catalyzed reactions e.g. hydrolysis of the materials in the biomass to lower molecular weight compounds e.g. hydrolyzates.

It is also believed possible that pressure will play a role and that the reaction may work with or without enzymes or acid catalysts at pressures associated with the temperature of between 100° C. and 200° C.

Therefore the largest operational range believed for the process is 20° C. to 200° C.

An advantage of this process is that it can be conducted without adding an inorganic acid preferably selected from the group consisting of sulfuric acid, hydrochloric acid, phosphoric acid, and the like, or mixtures thereof or without the addition lignin solubilizing organic solvents such as those selected from the group consisting of carbon, cetones and acetones of 2 to 6 carbon atoms and mixtures thereof, methanol, ethanol.

The reaction continues for a period time until the desired end point is reached. This period of time is known as the residence time or reaction time. While 5 minutes to 8 hours may be a preferred range, other preferred residence times are 5 minutes to 16 hours, 5 minutes to 24 hours, 5 minutes to 36 hours, 5 minutes to 48 hours, 5 minutes to 60 hours, and 5 minutes to 72 hours.

The residence time may cover a range of values. For example, the residence time may be greater than 8 hours and less than 72 hours being a preferred range, with greater than 8 hours and less than 60 hours being another preferred range, with greater than 8 hours and less than 48 hours another preferred range, with greater than 8 hours and less than 36 hours another preferred range, and with greater than 8 hours and less than 24 hours being another preferred range.

The residence time may also be established in a functional manner as the time it takes to reach the desired endpoint. In this instance, the desired endpoint may also be expressed as a percent of the biomasss available for hydrolysis. For example, if a 100 kg feedstock of biomass has 80 kg of biomass available for hydrolysis, the desired endpoint is preferably reached when 45% of the biomass available for hydrolysis has been hydrolyzed, or more preferably when 55% of the biomass available for hydrolysis has been reached, or even more preferably when 65% of the biomass available for hydrolysis has been reached.

After the desired reaction time is completed, the resulting hydrolyzed product (hydrolyzate) may be removed from the vessel and further processed.

In the batch process shown in FIG. 4, an amount of hydrolyzed product 6 is removed from the bottom of the vessel and placed into the second vessel 14 for further processing. The amount removed from vessel 13 is generally the same as the amount of materials introduced into the vessel, thus leaving solvent in the first vessel to be contacted with yet another batch of feedstock and catalyst composition. However, in one embodiment, vessel 13 may be completely emptied and the feedstock and solvent added to the vessel at or near the same time.

As shown in FIG. 4, feedstock stream 3, comprised of biomass and water, is supplied through feed line 1 to batch stirred tank reactor 13. The catalyst composition containing the catalyst(s) is supplied through feed line 2 to reactor 13. The feedstock and catalyst composition in phase 3 come into contact with the solvent phase 4, and are progressively hydrolyzed. While shown as three distinct phases, the phases will actually be present as a mixture throughout the vessel. After the desired amount of time, or residence time, or reaction time, the liquid hydrolyzate or product of hydrolysis or hydrolysis product is withdrawn from the reactor through valve 20 through product line 5, and fed to vessel 14 which could be used for the simultaneous saccharification and fermentation. The liquid hydrolyzate may not be completely liquid but may include some solids that have not yet been hydrolyzed and some solids which are not hydrolysable. The amount of the product removed is approximately equal to the amount of feedstock stream and catalyst composition introduced into vessel 13. The dashed lines between vessel 13 and 14 depict that the amount removed and placed into vessel 14 is approximately that of phase 3, i.e. the amount introduced into the vessel (phase 3). If the vessel is to be used for a second batch, the solvent stream left in the reactor (also known as the heel) will help speed up the reaction.

It should be apparent to one of skill in the art that the amount removed from batch to batch need not exactly match the amount charged at each batch to batch level, but the amount removed over a number of batches should be substantially equal to the amount charged otherwise the vessel will operate with the amount solvent too low or the vessel will overflow. As in the batch and continuous processes described herein, it is known that there are often variations in addition rates and product removal rates over time and batch to batch so that the terms "equal to" or "substantially equal to" are meant to include these variations.

A control parameter is the ratio of the weight of the solvent which includes the weight of the dispersed solids, pH buffers, catalyst(s), carriers, buffer control(s) and anything else in the solvent, to the weight of feedstock (the biomass plus water) in the feedstock at the moment of contact of the feedstock with the solvent.

There is expected to be a ratio below which there is no, or only a limited, effect upon the hydrolysis reaction. As a corollary, while there is theoretically no upper limit to the ratio, there is a point where additional solvent stream has little impact on the hydrolysis rate and merely increases the cost of the equipment through size and operating cost.

The amount of solvent used for a given amount of biomass is expected to depend at least upon the dry content amount of the biomass (a high dry content weight expected to require more solvent), the type of biomass and catalyst, the pH, the operating temperature and type of mixing employed.

The ratio of the weight of the solvent to the weight of the biomass plus water in the feedstock at the moment of contact is best explained by referring to the embodiments.

As shown in FIG. 1, the feedstock stream 3 comprised of biomass and water is supplied to continuous stirred tank reactor 10 through line 1. Catalysts, typically enzymes, are supplied as part of the catalyst composition introduced into reactor 10 through the line labeled 2. Inside vessel 10 is the solvent stream 4 of a known, or determinable weight. Since in the continuous stirred reactor, the residence time is such that the material exiting the reactor through line 5 is hydrolyzed to the desired point, the amount of solvent stream is the weight of the material in the vessel plus the amount in any recycle loops and recycle tanks at any given point in time. The biomass and catalyst are mixed with the solvent and the hydrolysis occurring at a very fast rate. The liquid reaction product (hydrolyzate) (6) is withdrawn from the reactor through product line 5. The amount of the liquid leaving the reactor through line 5 in a specified time is equal to the rate plus catalyst composition plus other materials that may have been added to vessel during the same specified period of time.

The ratio of the weight of the solvent to the weight of the biomass plus water in the feedstock at the moment of contact in this instance is the weight of the material in the vessel plus the amount in any recycle loops and recycle tanks that recirculate into the vessel (solvent) to the instantaneous addition rate of biomass plus water added to the vessel in common units of time. Those familiar with the continuous process will recognize this ratio as the residence time.

For example, a vessel contains 400 kg of solvent, for a residence time of 4 hrs. The feedstock is added at 100 kg/hr and the hydrolyzate product is removed at 100 kg/hr. The ratio is 400:100 or 4, or the residence time of 4 hrs. Therefore, for the CSTR the ratio is the residence time.

Figure 2:
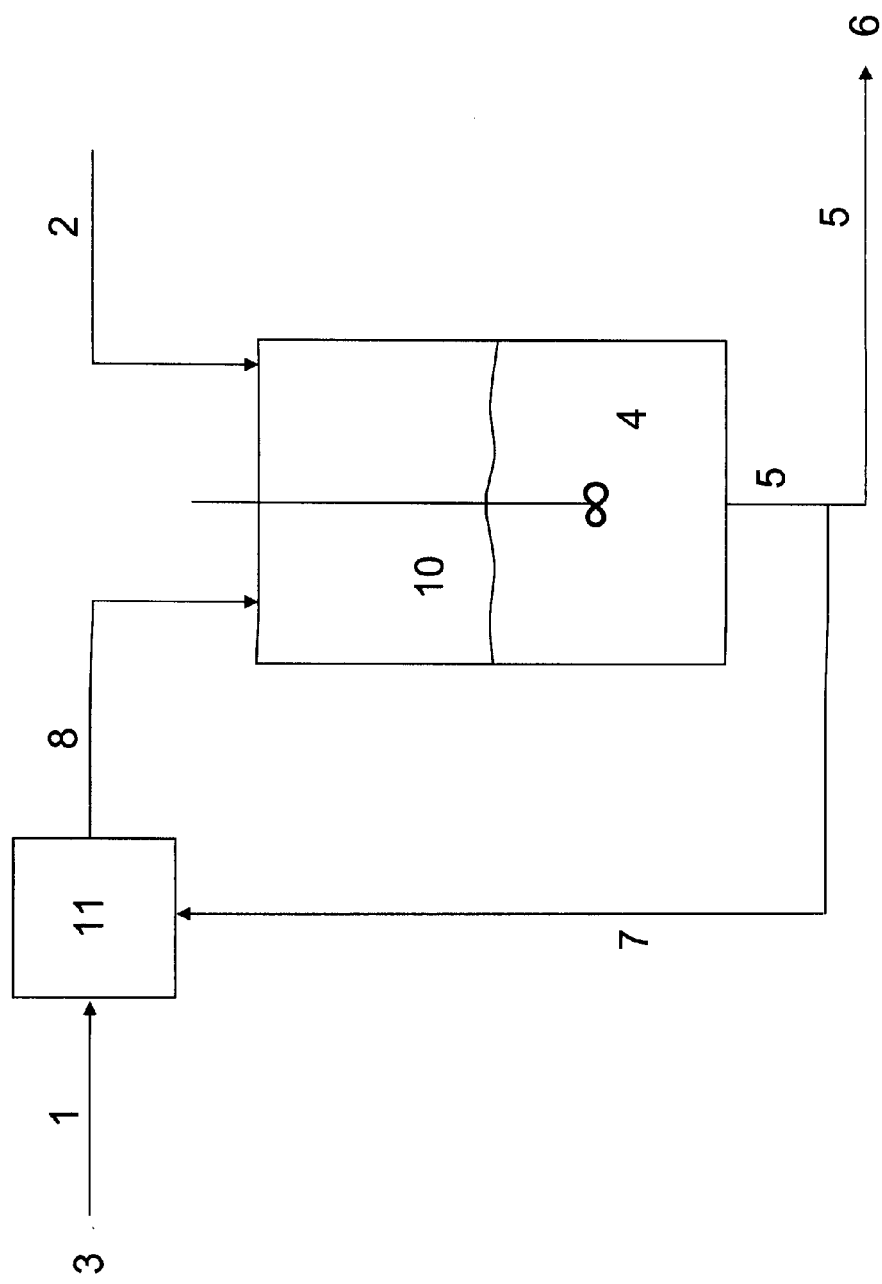
FIG. 2 is a schematic of a continuous hydrolysis process with a recycle loop.

FIG. 2 shows the process of FIG. 1 with a recycle stream. As shown in the figure, biomass and water are supplied through feed line 1 to premixer 11, where they are contacted with a portion of the solvent, liquid hydrolyzate incoming from line 7. The mixture is supplied through line 8 to a continuous stirred tank reactor 10. The catalyst composition is supplied through feed line 2 to reactor 10. Biomass is progressively hydrolyzed and the liquid hydrolyzate, or product 6 is withdrawn from the reactor through exit line 5, which is then split into recycle stream 7 and product line 5. The amount of material exiting the product line 5 over a specified period of time is equal to the rate plus catalyst composition plus other materials other than that coming from line 7, that are added to the vessel during the same specified period of time.

A further embodiment of the process is depicted in FIG. 5, and which can be translated to the embodiments shown is to separate some or all of the solids from the liquid hydrolyzate. Depending upon how complete the reaction is the solids can be optionally returned to the hydrolysis vessel 16 or vessel 15 for further hydrolysis. If the hydrolysis is substantially completed, the solids can be removed before passing the product stream to the next step.

Figure 7:
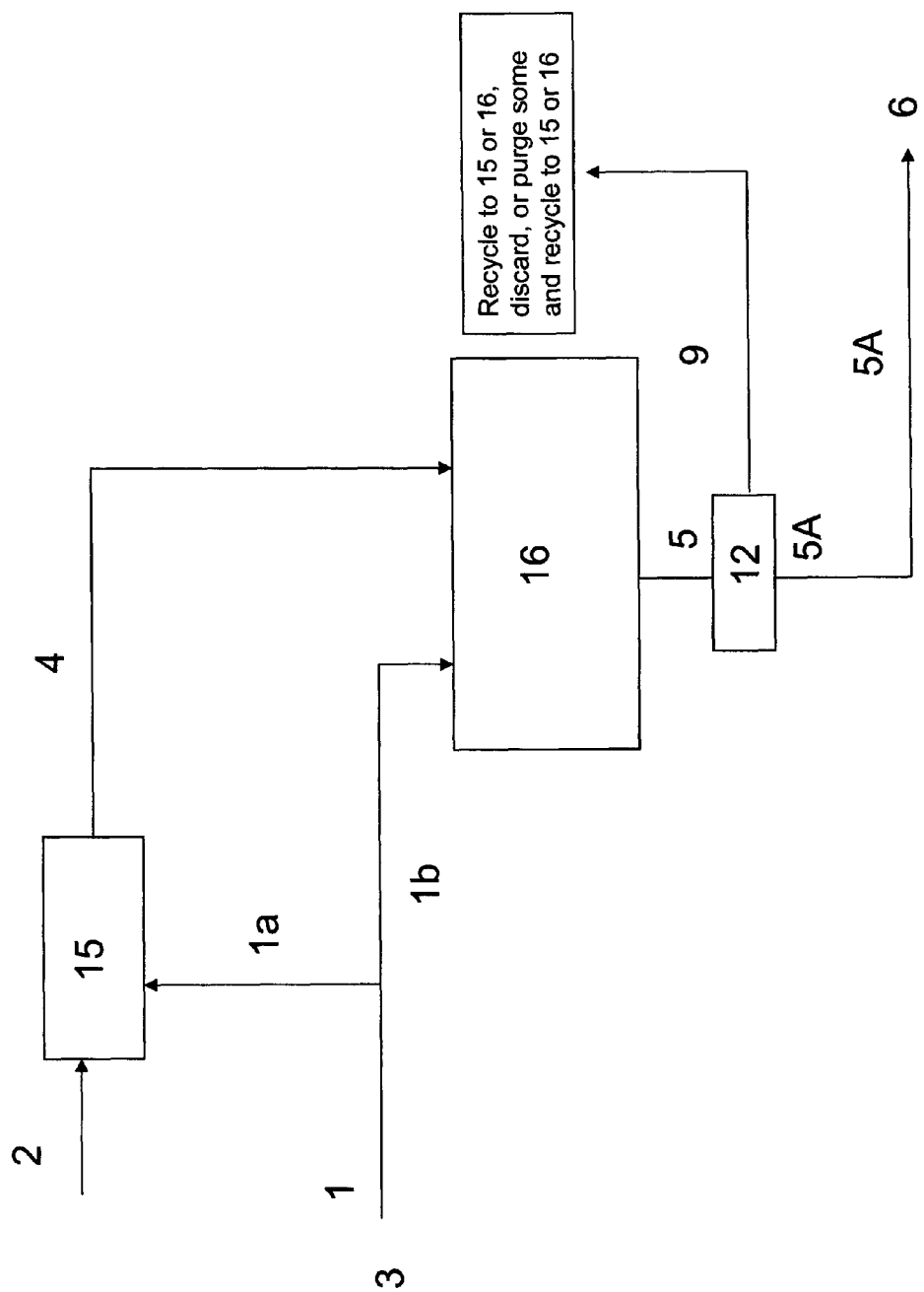
FIG. 7 is a schematic of a continuous hydrolysis process with separation of the solids in the hydrolysis product.

This improvement is shown in FIG. 7. In FIG. 7, stream 5 is fed to a solids separation device 12 to remove at least some of the solids and likely some of the liquid into solids stream 9 with stream 5A being the liquid stream with some solids removed. As indicated earlier, at least a portion of the solids stream may be optionally returned to the hydrolysis vessel 16 or vessel 15. The separation does not necessarily have to occur before taking the stream 9 before or after purging back to vessel 16 or 15, but preferably occurs prior to passing the product stream 6 onto the next step. As shown in FIG. 7, stream 9 may be recycled back into vessels 16 or 15, may be completely removed from the process, or a portion of stream 9 may be removed (purged) from the process and the remainder recycled back to either vessel 15, 16 or both.

Devices to separate solids from a liquid stream are well known in the art and include but are not limited to filters, cyclones, centrifuges, presses, decanters, gravity settling, skimmers and the like. A preferred separation device is selected from the group consisting of hydrocyclones and centrifuges.

Figure 3:
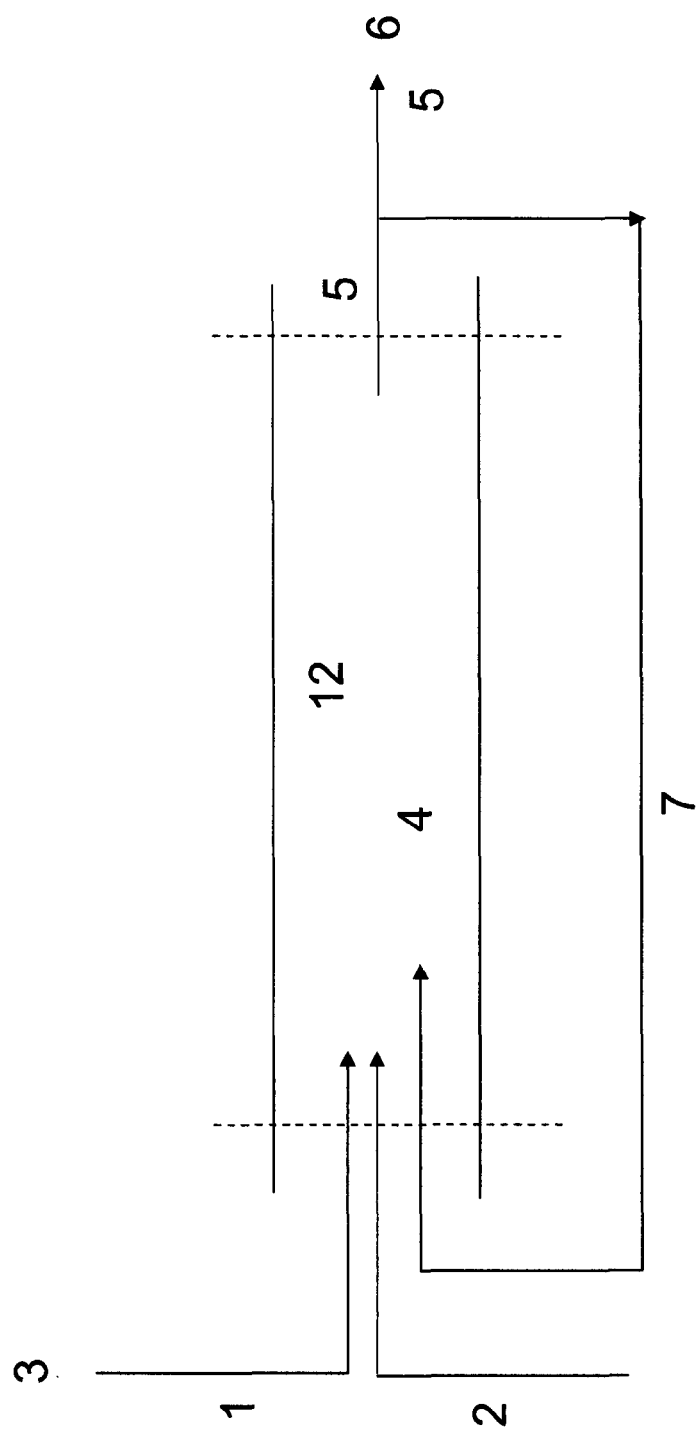
FIG. 3 is a schematic of a plug flow continuous process.

By analogy, one skilled in the art can modify the plug flow process of FIG. 3 to separate at least some of the solids from stream 5.

Simulations have demonstrated that by recycling the solids and passing the majority of the hydrolysis product on, the conversion rate for a given size vessel and residence time can be increased by as much as 400%.

The ratio of the weight of the solvent to the weight of the biomass plus water in the feedstock in this instance is the weight of the material in the vessel plus the amount of solvent added to premixer 11 in an hour to the weight of biomass plus water added to the vessel in one hour. Again, the residence time also expresses the ratio.

By similar analogy, there is the plug flow reactor embodiment as depicted in FIG. 3. Referring to FIG. 2, it is apparent that the process of FIG. 3 can be considered a "modification" of the process in FIG. 2 so that all the solvent of the stream is supplied through the premixer 11 and none is left in the vessel 10. As shown in FIG. 3, the feedstock stream 3 containing biomass and water is supplied through feed line 1 to a continuous plug flow reactor 12. The catalyst composition is supplied through feed line 2 to reactor 12. The solvent stream is added to the materials through feed line 7, which is diverted from line 5, which contains the hydrolyzed product. The ingredients form a slurry which is progressively hydrolyzed and liquid hydrolyzate 6 is withdrawn from the reactor through product line 5 and which splits into stream 7. The amount of product 6 removed per unit time (rate) is equal to the rate plus catalyst composition 2 plus all other materials other than that entering from line 7. The moment of contact is when the feedstock stream contacts the solvent stream. The ratio of the weight to the weight of the biomass plus water in the feedstock at the moment of contact in this instance is the weight of the material in stream 7 per unit time to the weight of biomass plus water added to the vessel per the same unit of time.

In the batch process shown in FIG. 4 and described previously, the ratio of the weight of the solvent to the weight of the biomass plus water in the feedstock at the moment of contact in this instance is the weight of the material in the vessel (the solvent stream marked as phase 4) to the weight of biomass plus water added per charge. If additional solvent is added, it would be added to the weight of 4 already in the reactor.

Should the batch process be modified to have a premixing of the biomass with the solvent, the ratio of the weight of the solvent to the weight of the biomass plus water in the feedstock at the moment of contact in this instance is the weight of the solvent in the vessel plus the weight of the solvent in the charge to the weight of biomass plus water added to the vessel per charge.

The values for the ratio of the weight solvent to the weight of the biomass plus water in the feedstock can vary from 1:99 to 100:1. However, it is more preferred that the range be from 5:95 to 95:5, or even more preferred from 10:90 to 90:10, with the ratio of 20:80 to 80:20 being more preferred with the range of 20:80 to 60:40 being most preferred, but with 10:90 to 90:10, 20:80 to 90:10, 30:70 to 90:10, 40:60 to 90:10, 50:50 to 90:10, and 60:40 to 90:10 also being suitable ranges.

The values for the ratio of the weight the solvent to the weight of the biomass plus water in the feedstock can also be expressed as a minimum ratio, since it is believed that there is no theoretical maximum value. Therefore, the ratio should be at least 0.8:1.0, or more preferably at least 1:1, or even more preferable at least 1.2:1, with at least 1.5:1 being more preferred, with 2:1 being even more preferred, and 3:1 being even more preferred.

Because the hydrolysis of cellulose is the central feature of the process, the ratio of the solvent to the weight of the biomass plus water in the feedstock may be substituted by the use of the cellulose and its hydrolysis products. As disclosed in the examples, none of the hydrolysis products were removed prior to the introduction of the next successive amount of feedstock. Thus, the ratio of the amount cellulose plus the amount of the products from hydrolyzed cellulose in the solvent to the amount of cellulose in the feedstock are the same as the ratios of the weight the solvent to the weight of the biomass plus water in the feedstock. The amount of cellulose in the feedstock and solvent are easily determinable. The amount of hydrolyzed products from cellulose can be determined by determining the products in the solvent and subtracting the amount of those products that come from hydrolysis of something other than cellulose or in the initial feedstock used to make the solvent. For example, starch also hydrolyzes to glucose and other hydrolysable species in common with cellulose. Therefore the amount of glucose and other hydrolysable species in common with cellulose in the solvent would have to be at least reduced by the amount that came from starch. This can be determined by knowing the amount of starch in the feed from which the solvent was made, the amount of starch in the solvent, with the difference being the amount of hydrolysable species coming from starch.

The controlling ratio can be expressed as a minimum ratio of the amount cellulose plus the amount of the products from hydrolyzed cellulose in the solvent to the amount of cellulose in the feedstock. This ratio should be at least 0.8:1.0, or more preferably at least 1:1, or even more preferable at least 1.2:1, with at least 1.5:1 being more preferred, with 2:1 being even more preferred, and 3:1 being even more preferred. The examples listed below would also establish a ratio of at least 4:1 and at least 5:1 as also working. It should be noted that in Example 5, while increasing the ratio decreased the hydrolysis time, the improvement was smaller with each additional amount of solvent. It should be pointed out that the ratio is exclusive to the cellulose and its hydrolysis products. Therefore, the glucose and products which are known hydrolysis products of cellulose that are present in the feedstock are to be substracted from those present in the solvent. Additionally, any products that were derived from the hydrolysis of hemicellulose or starch or other non-cellulosic material need subtracted from the solvent as well. This would include determining how much starch was reduced to glucose and substracting that glucose.

Because the solvent is best used prior to separation of anything other than insolubles, the relative composition the waters solubles in liquid portion of the solvent is the same as the relative composition of the water soluble products of the hydrolysis of the feedstock without separation of the water soluble components. While one can add water to dilute the water soluble components, their amounts relative to each other remain the same.

These above embodiments are not designed to limit the specification or claims, as there are many configurations available to one of ordinary skill, which include a series of continuous vessels, or semi batch reactors or in combination with or without plug flow reactors.

Figure 6:
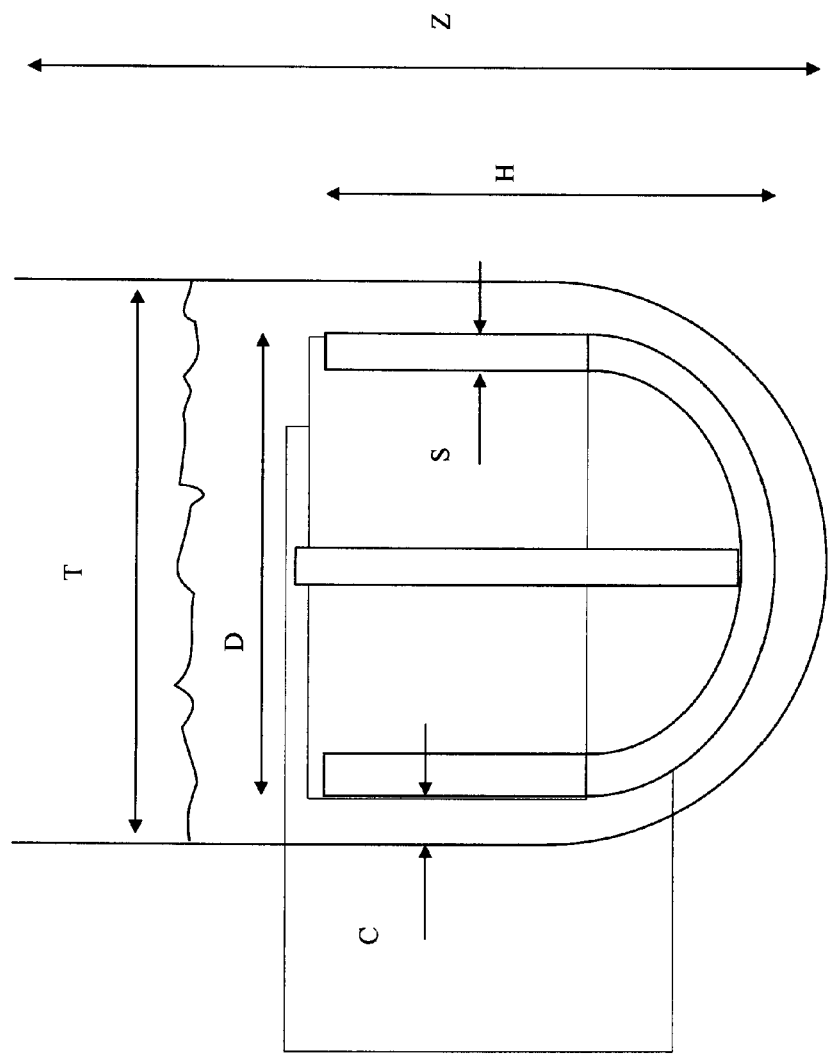
FIG. 6 depicts the type of apparatus used to conduct the experiments.

Experimental trials of viscosity reduction
Experimental apparatus 2 identical glass reactors, with the following geometric characteristics (see FIG. 6):
T (reactor diameter)=0.15 m
Z (reactor height)=0.30 m
jacket for heat exchange fluid all around the lateral surface and bottom, with a width of 4 cm;
hemi-spherical bottom;
cover with gasket and seal, with 5 openings (1 center hole for stirrer shaft; 4 side holes to add materials or for sampling, that during the tests will be closed with caps).

The two reactors are fitted with two different anchor agitators (A and B) to give the following configurations:
Configuration A:
("wingspan")=0,136 m
S (blade width)=0.01 m
H (anchor height)=0.12 cm
C (clearance, blade-wall distance)=0.007 m
D/T=0.907
D/S=13.6
T/S=15

Configuration B:
in this configuration, the blades are inclined at 45 degrees for better scrape the wall
D ("wingspan")=0,145 m
LS (blade width)=0.0141 m
S (projection blade width)=0.01 m
H (anchor height)=0,145 cm
C (clearance, blade-wall distance)=0.0025 m
D/T=0.967
D/S=14.5
T/S=15

Agitation is provided by Heidolph RZR 2102 control motors (power: 140 W).

Two thermal baths ensure the maintenance of temperature by circulating water at 45° C. in the reactor jackets.

Materials

The starting materials used are pre-treated Sorgo and Arundo Donax. The materials were stored at −18° C. to prevent degradation.

The characteristics of starting materials are as follows:

|  |  |  | Sorghum | Arundo |
|---|---|---|---|---|
|  | dry content | % wt. | 20.41% | 30.39% |
|  | WIS | % wt. | 16.01% | 24.51% |
|  | WSS | % wt. | 4.40% | 5.88% |
|  | solubilised solids/total solids | % wt. | 21.58% | 19.34% |
| liquid fraction | water | % wt. | 79.59% | 69.61% |
|  | glucose | % wt. | 0.03% | 0.10% |
|  | xylose | % wt. | 0.34% | 1.19% |
|  | cellobiose | % wt. | 0.00% | 0.00% |
|  | galactose | % wt. | 0.00% | 0.00% |
|  | arabinose | % wt. | 0.00% | 0.00% |
|  | formic acid | % wt. | 0.00% | 0.00% |
|  | acetic acid | % wt. | 0.28% | 0.58% |
|  | 5-HMF | % wt. | 0.01% | 0.05% |
|  | furfural | % wt. | 0.04% | 0.19% |
|  | levulinic acid | % wt. | 0.00% | 0.00% |
|  | lactic acid | % wt. | 0.00% | 0.00% |
|  | glucolygomers | % wt. | 0.23% | 0.22% |
|  | xylolygomers | % wt. | 1.48% | 1.96% |
|  | galactolygomers | % wt. | 0.00% | 0.00% |
|  | arabinolygomers | % wt. | 0.00% | 0.00% |
|  | solubilised acetyl groups | % wt. | 0.11% | 0.29% |
|  | other solubilised | % wt. | 1.89% | 1.30% |
| solid fraction | glucans | % wt. | 9.01% | 13.65% |
|  | xylans | % wt. | 1.16% | 1.26% |
|  | galactans | % wt. | 0.00% | 0.00% |
|  | arabinans | % wt. | 0.00% | 0.00% |
|  | unsolubilised acetyl groups | % wt. | 0.12% | 0.22% |
|  | klason lignin | % wt. | 5.29% | 8.90% |
|  | other unsolubilised | % wt. | 0.42% | 0.48% |
|  | Total | % wt. | 100.00% | 100.00% |

WIS is the water unsolubilised solid percentage (on the total material).

WSS is the water solubilised solid percentage (on the total material).

The sum of WSS and WIS is equal to the dry content value.

The compositional characteristics were determined using standard analytical methods, the followed procedures are:

Determination of Structural Carbohydrates and Lignin in Biomass

Laboratory Analytical Procedure (LAP) Issue Date: Apr. 25, 2008

Technical Report NREL/TP-510-42618 Revised April 2008

Determination of Extractives in Biomass

Laboratory Analytical Procedure (LAP) Issue Date: Jul. 17, 2005

Technical Report NREL/TP-510-42619 January 2008

Preparation of Samples for Compositional Analysis

Laboratory Analytical Procedure (LAP) Issue Date: Sep. 28, 2005

Technical Report NREL/TP-510-42620 January 2008

Determination of Total Solids in Biomass and Total Dissolved Solids in Liquid Process Samples Laboratory Analytical Procedure (LAP) Issue Date: Mar. 31, 2008

Technical Report NREL/TP-510-42621 Revised March 2008

Determination of Ash in Biomass

Laboratory Analytical Procedure (LAP) Issue Date: Jul. 17, 2005

Technical Report NREL/TP-510-42622 January 2008

Determination of Sugars, Byproducts, and Degradation Products in Liquid Fraction Process Samples Laboratory Analytical Procedure (LAP) Issue Date: Dec. 8, 2006

Technical Report NREL/TP-510-42623 January 2008

Determination of Insoluble Solids in Pretreated Biomass Material

Laboratory Analytical Procedure (LAP) Issue Date: Mar. 21, 2008

Technical Report NREL/TP-510-42627 March 2008

The enzyme cocktail used has the following characteristics, maintained constant for all tests:

| Component | volumetric composition % | density g/ml | specific activity |
|---|---|---|---|
| cellulase complex | 87.4% | 1.08 | 100 FPU/$g_{component}$ |
| xylanase | 5.3% | 1.2 | 500 FXU/$g_{component}$ |
| hemicellulase | 6.6% | 1.1 | 470 FXU/$g_{component}$ |
| enzyme complex | 0.7% | 1.2 | 100 FBG/$g_{component}$ |
| Total | 100.0% | 1.09 | |

The cellulase complex enzyme preparation is a solution that catalyzes the breakdown of cellulosic material to glucose, cellobiose and gluco-oligomers of higher molecular weight. The enzymatic solutions hemicellulase and xylanase catalyze mainly the hemi-cellulose depolymerisation to its constituents in the form of simple sugars or oligomers; moreover, they show side catalytic activities to a lesser extent.

The enzyme complex is an enzyme solution that acts on various carbohydrates and shows the ability to enhance the activity of the solution thus prepared.

The described cocktail has the following activities:

| Enzymatic cocktail activity | |
|---|---|
| 94.39 FPU/ml | 86.60 FPU/g |
| 65.92 FXU/ml | 60.48 FXU/g |
| 0.84 FBG/ml | 0.77 FBG/g |

FPU is measured and defined according to the NREL Laboratory Analytical Procedure (Technical Report NREL/TP-510-42628, January 2008). This method uses the industry standard and measures the cellulose activity in terms of "filter paper units" (FPU) per milliliter of original (undiluted) enzyme solution. For quantitative results the enzyme preparations must be compared on the basis of significant and equal conversion. One filter paper unit for a given enzyme is the amount of enzyme needed to release 2.0 mg of reducing sugar as glucose from 50 mg of filter paper from a Whatman No. 1 filter strip (4% conversion) in 60 minutes at 50° C. and has been designated as the intercept for calculating filter paper cellulose units (FPU) by International Union of Pure and Applied Chemistry (IUPAC) guidelines.

Xylanase activity in FXU is measured relative to an enzyme standard with a known activity. A spectrophotometer measure on the supernatant described below is compared to a standard curve obtained by standard samples.

Xylanase samples are incubated with a remazol-stained wheat arabinoxylan substrate. Unconverted substrate is precipitated with ethanol. The intensity of blue colouring of the supernatant due to unprecipitated remazol-stained substrate degradation products is proportional to the endoxylanase activity. The colour profile may vary from enzyme to enzyme.

$$\text{Sample activity } (FXU/g) = \frac{W}{C \cdot F \cdot D}$$

Where:
C is enzyme activity read from the standard curve (FXU/ml)
F is volume of sample (ml)
D is further dilution of sample (e.g. second or third dilution)
W is weight of sample (g)

One FBG is the amount of enzyme which, according to the standard procedure (Somogyi Nelson method) described below, releases glucose or reducing carbohydrate with a reduction capacity equivalent to 1 mol glucose per minute.

Standard reaction conditions:
A sample should be diluted to give an activity between 0.02-0.10 FBG/ml.
Substrate: 0.5% beta glucan
Temperature: 30° C.
pH: 5.0
Reaction time: 30 min Fungal beta glucanase reacts with beta glucan during the formation process to glucose or reducing carbohydrate which is determined as reducing sugar.

Moreover, to maintain the pH to a value of about 5, since it is not possible to use a pH meter (due to the nature of the material), a 1N buffer solution of citrate, for a total amount of 1% on the loaded material quantity, is used.

Test No. 1

Material: Sorghum (described above).

The reactors were fitted (including mixers) and the heat exchange fluid is brought to temperature (45° C.). The 2 engines were calibrated so as to provide (without material, with only the stirring inertia) at a stirring speed of 12 rpm (minimum speed of the instrument), a torque value equal to 0.0 N·cm.

Both reactors were filled with 1.5 kg of material just thawed, and the stirring rate was started in order to homogenize the material. In none of the 2 reactors free water was visible. The density of the material in these conditions was approximately equal to 600 kg/m³. Both systems of agitation, at 12 rpm, indicated an overload (the provided torque value was out of the measuring scale, at more than 200 N·cm).

At time t=0, in both reactors a solution (total weight about 96 g) composed as follows was added:
29.4 ml of enzyme cocktail with the composition described above, determined to provide an activity of the cellulase complex of 20 FPU/g glucans (meaning glucans as the sum of cellobiose and gluco-oligomers in the liquid phase and glucans in the solid phase), and other activities are provided as a consequence. This 20 FPU/g glucans is approximately 9 FPU/g total dry matter, calculated on the cellulose content of the feedstock.
16.5 grams of buffer solution (citrate) as described above and determined to be about 1% of the total material.
48.5 grams of $H_2O$, in order to dilute the enzyme solution and improve its dispersion; the amount of water to be added is determined so that the total solution to be added ($H_2O$+cocktail+citrate) is equal to about 30% of the dry content of the initial pre-treated material.

After the addition, in each reactor there were 1.6 kg of total material, with a dry content (calculated) of about 19.2%. The presence of condensation under the cover suggests that the dry content could actually be higher. The stirring rate was increased to about 180 rpm (for a while) to mix the material and the added solution. At this point, there was no free water, and the level of the material in the reactor was the same as before (at this stage, estimated density was about 650 kg/m³).

Both reactions were carried out in parallel, maintaining the agitation speed the same in both cases, the stirring rate was set equal to 12 rpm for the first hour, then raised to a value of 100 rpm. Every 60 minutes, the stirring rate was raised to 180 rpm (for a few seconds) in order to homogenize the material.

Throughout the test, the measured torque on the engine of the reactor A is always lower than the B one. After about 5 hours, the material in the reactor A had an appearance of liquid (torque values of about 20 N·cm at 100 rpm), while the other (although the reaction occurred in part, as evidenced by the fact that the torque had dropped to values of about 140 N·cm at 100 rpm, from more than 200 N·cm initials) had a solid appearance.

After a further hour (t=6 h), in which the conditions in the two reactors are not substantially changed, all the material of the reactor B (which had a negligible release of free liquid, but still had a solid appearance) was inserted in the reactor A. After the addition, agitation was set equal to 200 rpm for few seconds in order to homogenize the material, and then set equal to 100 rpm, with a torque of 120 N·cm, and the appearance of the material of a very wet solid. In about 10 minutes, the measured torque value has dropped to 20 N·cm, and the material assumed the aspect of a liquid, similar to the one present in the reactor A before addition. The test was stopped after 10 minutes more, when the torque had fallen to about 15 N·cm at 100 rpm. The density of the material, measured at this point, was approximately 1100 kg/m$^3$.

Test No. 2.

Material: Sorghum (described above).

The reactors were fitted (including mixers) and the heat exchange fluid is brought to temperature (45° C.). The 2 engines were calibrated so as to provide (without material, with only the stirring inertia) at a stirring speed of 12 rpm (minimum speed of the instrument), a torque value equal to 0.0 N·cm.

In trial No. 2, in the A reactor, a test under the same conditions of test No. 1 (conducted in the same reactor) was carried out, with similar results.

The B reactor, was filled with 1.5 kg of material coming from the test No. 1 (liquid aspect, density of 1100 kg/m$^3$, measured torque at 100 rpm equal to about 15 N·cm). To this material, 1.5 kg of sorghum pretreated (with the characteristics described in the previous section, in particular dry content equal to 20.41%) and the same solution utilized in the test No. 1 (about 96 g total) were added. The dry content, after the various additions, was calculated to be equal to 19.2%. The presence of condensation under the cover suggests that the actual dry content could be higher. The stirring rate was increased to about 150 rpm (for a while) to mix the material. At this point, the homogenized material had an apparent density of about 800 kg/m$^3$, and a torque value equal, at 100 rpm, to about 150 N·cm.

Both reactions were carried out in parallel, maintaining the agitation speed the same in both cases, the stirring rate was set equal to 12 rpm for the first hour, then raised to a value of 100 rpm. Every 60 minutes, the stirring rate was raised to 180 rpm (for a few seconds) in order to homogenize the material.

During the test No. °2, in the reactor B a significantly better result was achieved respect to the test No. 1, in which after 6 h liquefaction was not yet reached. In particular, after about 3 h (a time lower than the one needed in the reactor A), the material had a liquid appearance, with a value of torque at 100 rpm equal to about 20 N·cm (while in the reactor A, the measured value was about 100 N·cm, and the material had an appearance of a wet solid). After about 7 hours of testing, the material in the two reactors had a similar appearance, but the result was reached in the reactor B in about 60% of the time.

Compositional analysis tests on the material obtained in the reactor B (after 7 h) showed an enzymatic hydrolysis yield on glucose (respect to the total glucans) equal to about 25% and on xylose (respect to the total xylans) equal to approximately 50%. These values are higher than those obtained in earlier trials of viscosity reduction.

Furthermore, on the final material a measure of pH was performed, and it was found to be equal to 3.9. This value is lower than the one that, according to the literature data, ensures the highest enzyme activity (pH=5).

Test No. 3

Material: Arundo Donax (described above).

The procedure followed in the test No. 3 was the same one used in the test No. 1 (trials with Sorghum).

In the two reactors, each filled with 1.5 kg of pretreated Arundo (measured dry content equal to 30.4%), no free water was visible. The density of the material in these conditions was approximately equal to 600 kg/m$^3$. Both systems of agitation, at 12 rpm, indicated an overload At time t=0, in both reactors a solution (total weight about 140 g composed as follows was added:

44.1 ml of enzyme cocktail with the composition described above, determined to provide an activity of the cellulase complex of 20 FPU/g glucans (meaning glucans as the sum of cellobiose and gluco-oligomers in the liquid phase and glucans in the solid phase), and other activities are provided as a consequence.

17.3 grams of buffer solution (citrate) as described above and determined to be about 1% of the total material.

78.4 grams of H$_2$O, in order to dilute the enzyme solution and improve its dispersion; the amount of water to be added is determined so that the total solution to be added (H$_2$O+cocktail+citrate) is equal to about 30% of the dry content of the initial pre-treated material.

After the addition, in each reactor there were 1.6 kg of total material, with a dry content (calculated) of about 27.8%. The presence of condensation under the cover suggests that the dry content could actually be higher. The stirring rate was increased to about 180 rpm (for a while) to mix the material and the added solution. At this point, there was no free water, and the level of the material in the reactor was the same as before (at this stage, estimated density was about 650 kg/m$^3$).

Both reactions were carried out in parallel, maintaining the agitation speed the same in both cases, the stirring rate was set equal to 12 rpm for the first hour, then raised to a value of 100 rpm. Every 60 minutes, the stirring rate was raised to 180 rpm (for a few seconds) in order to homogenize the material.

Throughout the test, the measured torque on the engine of the reactor A is always lower than the B one. After about 6.5 hours, the material in the reactor A had an appearance of liquid (torque values of about 20 N·cm at 100 rpm), while the other (although the reaction occurred in part, as evidenced by the fact that the torque had dropped to values of about 140 N·cm at 100 rpm, from more than 200 N·cm initials) had a solid appearance.

After further 30 minutes, in which the conditions in the two reactors are not substantially changed, all the material of the reactor B (which had a negligible release of free liquid, but still had a solid appearance) was inserted in the reactor A. After the addition, agitation was set equal to 200 rpm for few seconds in order to homogenize the material, and then set equal to 100 rpm, with a torque of 130 N·cm, and the appearance of the material of a very wet solid. In about 20 minutes, the measured torque value has dropped to 20 N·cm, and the material assumed the aspect of a liquid, similar to the one present in the reactor A before addition. The test was stopped after 40 minutes more, when the torque had fallen to about 15 N·cm at 100 rpm. The density of the material, measured at this point, was approximately 1100 kg/m$^3$.

Test No. 4

Material: Arundo Donax (described above).

The procedure followed in the test No. 4 was the same one used in the test No. 2 (trials with Sorghum).

In trial No. 4, in the A reactor, a test under the same conditions of test No. 3 (conducted in the same reactor) was carried out, with similar results.

The B reactor was filled with 1.5 kg of material coming from the test No. 3 (liquid aspect, density of 1100 kg/m³, measured torque at 100 rpm equal to about 15 N·cm). To this material, 1.5 kg of pretreated arundo (with the characteristics described in the previous section, in particular dry content equal to 30.4%) and the same solution utilized in the test No. 3 (about 140 g total) were added. The dry content, after the various additions, was calculated to be equal to 27.8%. The presence of condensation under the cover suggests that the actual dry content could be higher. The stirring rate was increased to about 150 rpm (for a while) to mix the material. At this point, the homogenized material had an apparent density of about 750 kg/m³, and a torque value equal, at 100 rpm, to about 170 N·cm.

Both reactions were carried out in parallel, maintaining the agitation speed the same in both cases, the stirring rate was set equal to 12 rpm for the first hour, then raised to a value of 100 rpm. Every 60 minutes, the stirring rate was raised to 180 rpm (for a few seconds) in order to homogenize the material.

During the test No. 4, in the reactor B a significantly better result was achieved respect to the test No. 3, in which after 7 h liquefaction was not yet reached. In particular, after about 5 h (a time lower than the one needed in the reactor A), the material had a liquid appearance, with a value of torque at 100 rpm equal to about 20 N·cm (while in the reactor A, the measured value was about 90 N·cm, and the material had an appearance of a wet solid). After about 8 hours of testing, the material in the two reactors had a similar appearance, but the result was reached in the reactor B in about 75% of the time.

Test No. 5

Material: Arundo Donax (described above

The B reactor was filled with 1.5 kg of material coming from the test No. 3 (liquid aspect, density of 1100 kg/m³, measured torque at 100 rpm equal to about 15 N·cm). To this material, 0.5 kg of pretreated arundo (with the characteristics described in the previous section, in particular dry content equal to 30.4%) were added.

At time t=0, in both reactors a solution (total weight about 46.5 g), composed as follows, was added:
- 14.7 ml of enzyme cocktail with the composition described above, determined to provide an activity of the cellulase complex of 20 FPU/g glucans (meaning glucans as the sum of cellobiose and gluco-oligomers in the liquid phase and glucans in the solid phase), and other activities are provided as a consequence.
- 28.8 grams of buffer solution (citrate) as described above and determined to be about 5% of the total material.
- 3.1 grams of $H_2O$, in order to dilute the enzyme solution and improve its dispersion; the amount of water to be added is determined so that the total solution to be added ($H_2O$+cocktail+citrate) is equal to about 30% of the dry content of the initial pre-treated material.

After the addition, in the reactor there were 2.05 kg of total material, with a dry content (calculated) of about 27.8%. The presence of condensation under the cover suggests that the dry content could actually be higher. The stirring rate was increased to about 150 rpm (for a while) to mix the material and the added solution. At this point, the homogenized material had an apparent density of about 900 kg/m3, and a torque value equal at 100 rpm to about 150 N·cm.

The reaction was carried out maintaining the stirring rate equal to 100 rpm for the first hour, Every 20 minutes, the stirring rate was raised to 180 rpm (for a few seconds) in order to homogenize the material.

After about 65 minutes, the material had a liquid appearance (torque values of about 30 N·cm at 100 rpm). The estimated density was around 1100 kg/m³.

At this point, to the material in the reactor 500 g of pretreated Arundo Donax and 46.5 g of the solution described above were added. After the addition, in the reactor there were about 2.6 kg of total material, with a percentage of dry (calculated) of about 27.8%. The presence of condensation under the cover suggests that the dry content could actually be higher. The stirring rate was increased to about 150 rpm (for a while) to homogenize the material, that had an apparent density of about 950 kg/m³, and a torque value equal at 100 rpm to about 120 N·cm.

After about 45 minutes, the material had a liquid appearance (torque values of about 30 N·cm at 100 rpm). The estimated density was around 1100 kg/m3.

At this point, to the material in the reactor 500 g of pretreated Arundo Donax and 46.5 g of the solution described above were added. After the addition, in the reactor there were about 3.15 kg of total material, with a percentage of dry (calculated) of about 27.8%. The presence of condensation under the cover suggests that the dry content could actually be higher.

The stirring rate was increased to about 150 rpm (for a while) to homogenize the material, that had an apparent density of about 950 kg/m³, and a torque value equal at 100 rpm to about 120 N·cm.

After about 35 minutes, the material had a liquid appearance (torque values of about 30 N·cm at 100 rpm). The estimated density was around 1100 kg/m³.

The test was stopped after approximately 8 hours. The liquefaction of 1.5 kg of pretreated material was globally achieved in 2 h and 25 minutes, a time equal to about 50% of the time taken by the reactor B in the test No. 4 and to about 38% of the time required by the reactor A in tests No. 3 and No. 4.

Test No. 6

Material: Sorghum (described above).

The reactors were fitted (including mixers) and the heat exchange fluid is brought to temperature (45° C.). The 2 engines were calibrated so as to provide (without material, with only the stirring inertia) at a stirring speed of 12 rpm (minimum speed of the instrument), a torque value equal to 0.0 N·cm.

In trial No. 6, in the B reactor, a test under the same conditions of test No. 2 (conducted in the same reactor) was carried out, with similar results.

The A reactor was filled with 0.75 kg of pre-treated sorghum (characteristics described in the previous section, in particular dry content equal to 20.4%). To the solid, which had a density of about 600 kg/m³, a solution (total weight about 96 g) composed as follows was added:
- 29.4 ml of enzyme cocktail with the composition described above, determined to provide an activity of the cellulase complex of 40 FPU/g glucans (meaning glucans as the sum of cellobiose and gluco-oligomers in the liquid phase and glucans in the solid phase), and other activities are provided as a consequence. This 40 FPU/g glucans is approximately 18 FPU/g total dry matter, calculated on the cellulose content of the feedstock.
- 16.5 grams of buffer solution (citrate) as described above and determined to be about 2% of the total material.
- 48.5 grams of $H_2O$, in order to dilute the enzyme solution and improve its dispersion; the amount of water to be added is determined so that the total solution to be added ($H_2O$+cocktail+citrate) is equal to about 60% of the dry content of the initial pre-treated material.

In this way, the A reactor worked with a load of enzyme per gram of glucans twice respect to tests No. 1 and No. 2. Moreover, the initial dry content was calculated to be equal to 17.5% (lower than the one calculated in tests No. 1 and No. 2). The presence of condensation under the cover suggests that the dry content could actually be higher.

The stirring rate was increased to about 180 rpm (for a while) to mix the material and the added solution. The apparent density of the obtained material was about 700 kg/m3, and the measured torque at 100 rpm was equal to about 160 N·cm.

Both reactions were carried out in parallel, maintaining the agitation speed the same in both cases, the stirring rate was set equal to 12 rpm for the first hour, then raised to a value of 100 rpm. Every 60 minutes, the stirring rate was raised to 180 rpm (for a few seconds) in order to homogenize the material.

In this test, in the reactor A, a significantly better result was achieved respect to the test No. 1 and No. 2 (performed in the same reactor) and also respect to the reaction conducted in the reactor B. In particular, after about an hour, the material had a liquid appearance (apparent density of about 1000 -1100 kg/m$^3$), with a value of torque at 100 rpm at about 20 N·cm. At the same time, in the reactor B, the material had the appearance of wet solid, with a value of torque at 100 rpm equal to about 100 N·cm.

At this point, in the reactor A 750 g of sorghum pretreated were further added (as described in the previous section, dry content equal to 20.41%). As a result of this addition, the calculated dry content came back to the value of the previous tests, 19.2%, and the load of enzyme per gram of cellulose was reduced to the value of the previous tests (20 FPU/g glucans). The stirring rate was increased to about 150 rpm (for a while) to mix the material. At this point, the homogenized material had an apparent density of about 800 kg/m$^3$, and a torque value equal, at 100 rpm, to about 120 N·cm.

After a further hour of stirring, the material had a liquid appearance again, with values of density and torque equal to about the same as the ones measured before the addition. After about 7 h of testing, the material had a similar appearance similar in both the reactors, but in the A reactor had reached a liquid state in about 65% of the time needed in the B and about 39% of time needed by the reactor A in tests No. 1 and No. 2.

Test No. 7

Material: Arundo Donax (described above).

In trial No. 7, in the B reactor, a test under the same conditions of test No. 4 (conducted in the same reactor) was carried out, with similar results.

The A reactor was filled with 0.75 kg of pre-treated arundo (characteristics described in the previous section, in particular dry content equal to 30.4%). To the solid, which had a density of about 600 kg/m$^3$, a solution (total weight about 140 g) composed as follows was added:

- 44.1 ml of enzyme cocktail with the composition described above, determined to provide an activity of the cellulase complex of 40 FPU/g glucans (meaning glucans as the sum of cellobiose and gluco-oligomers in the liquid phase and glucans in the solid phase), and other activities are provided as a consequence.
- 17.3 grams of buffer solution (citrate) as described above and determined to be about 2% of the total material.
- 78.4 grams of $H_2O$, in order to dilute the enzyme solution and improve its dispersion; the amount of water to be added is determined so that the total solution to be added ($H_2O$+cocktail+citrate) is equal to about 60% of the dry content of the initial pre-treated material.

In this way, the A reactor worked with a load of enzyme per gram of glucans twice respect to tests No. 3 and No. 4. Moreover, the initial dry content was calculated to be equal to 25.6% (lower than the one calculated in tests No. 3 and No. 4). The presence of condensation under the cover suggests that the dry content could actually be higher.

The stirring rate was increased to about 150 rpm (for a while) to mix the material and the added solution. The apparent density of the obtained material was about 750 kg/m3, and the measured torque at 100 rpm was equal to about 180 N·cm.

Both reactions were carried out in parallel, maintaining the agitation speed the same in both cases, the stirring rate was set equal to 12 rpm for the first hour, then raised to a value of 100 rpm. Every 60 minutes, the stirring rate was raised to 180 rpm (for a few seconds) in order to homogenize the material.

In this test, in the reactor A, a significantly better result was achieved respect to the test No. 3 and No. 4 (performed in the same reactor) and also respect to the reaction conducted in the reactor B. In particular, after about 2.5 hours, the material had a liquid appearance (apparent density of about 1000 -1100 kg/m$^3$), with a value of torque at 100 rpm at about 20 N·cm. At the same time, in the reactor B, the material had the appearance of wet solid, with a value of torque at 100 rpm equal to about 130 N·cm.

At this point, in the reactor A 750 g of pretreated arundo were further added (as described in the previous section, dry content equal to 30.4%). As a result of this addition, the calculated dry content came back to the value of the previous tests, 27.8%, and the load of enzyme per gram of cellulose was reduced to the value of the previous tests (20 FPU/g glucans). The stirring rate was increased to about 150 rpm (for a while) to mix the material.

After further 1.5 hours of stirring, the material had a liquid appearance again, with values of density and torque equal to about the same as the ones measured before the addition. After about 8 h of testing, the material had a similar appearance similar in both the reactors, but in the A reactor had reached a liquid state in about 80% of the time needed in the B and about 57% of time needed by the reactor A in tests No. 3 and No. 4.

On the final material a measure of pH was performed, and it was found to be equal to 2.4. This value is lower than the one that, according to the literature data, ensures the highest enzyme activity (pH=5).

Test No. 8

Material: Arundo Donax (described above).

The A reactor was filled with 1.5 kg of material coming from the test No. 7 (liquid aspect, density of 1100 kg/m$^3$, measured torque at 100 rpm equal to about 15 N·cm). To this material, 0.75 kg of pretreated arundo (with the characteristics described in the previous section, in particular dry content equal to 30.4%) were added.

About 140 g of solution used in the test n°7 were added to material. After the addition, in the reactor there were 2.4 kg of total material.

In this way, the reactor worked with a load of enzyme per gram of glucans twice respect to tests No. 3 and No. 4. Moreover, the initial dry content was calculated to be equal to 25.6% (lower than the one calculated in tests No. 3 and No. 4). The presence of condensation under the cover suggests that the dry content could actually be higher.

The stirring rate was increased to about 150 rpm (for a while) to mix the material and the added solution. The apparent density of the obtained material was about 850 kg/m3, and the measured torque at 100 rpm was equal to about 150 N·cm.

The reaction was carried out maintaining the stirring rate was set equal to 100 rpm. Every 20 minutes, the stirring rate was raised to 180 rpm (for a few seconds) in order to homogenize the material.

In particular, after about 2 hours, the material had a liquid appearance (apparent density of about 1000-1100 kg/m$^3$), with a value of torque at 100 rpm at about 25 N·cm.

At this point, in the reactor 750 g of pretreated arundo were further added (as described in the previous section, dry content equal to 30.4%), and the total amount of material was 3.15 kg. As a result of this addition, the calculated dry content came back to the value of the previous tests, 27.8%, and the load of enzyme per gram of cellulose was reduced to the value of the previous tests (20 FPU/g glucans). The presence of condensation under the cover suggests that the dry content could actually be higher. The stirring rate was increased to about 150 rpm (for a while) to mix the material.

At this point, the homogenized material had an apparent density of about 900 kg/m3, and a torque value equal to 100 rpm to about 135 N·cm.

After further 1 hour of stirring, the material had a liquid appearance again, with an apparent value of density equal to about 1100 kg/m$^3$ and torque equal to about 25 N·cm at 100 rpm. After about 8 h of testing, the material had a similar appearance similar in both the reactors, but in the A reactor had reached a liquid state in about 80% of the time needed in the B and about 57% of time needed by the reactor A in tests No. 3 and No. 4.

The test was conducted approximately for 8 hours.

The liquefaction of 1.5 kg of pretreated material was globally achieved in 3 h, a time equal to about 75% of the time taken by the reactor in the test No. 7.

We claim:

1. A process for the hydrolysis of ligno-cellulosic biomass comprising the steps of
    A) contacting a ligno-cellulosic feedstock of a feedstock stream, the ligno-cellulosic feedstock comprised of a ligno-cellulosic biomass having a dry content and water, with at least a portion of a solvent, wherein the dry content comprises cellulose, hemicellulose, and the weight percent of the cellulose in the dry content is greater than 5 weight percent of the dry content, the solvent comprises water soluble hydrolyzed species; wherein at least some of the water soluble hydrolyzed species are the same as the water soluble hydrolyzed species obtainable from the hydrolysis of the cellulose in the feedstock;
    B) maintaining the contact between the feedstock of the feedstock stream and the solvent in the presence of a catalyst composition for the hydrolysis of the cellulose comprising at least one cellulase enzyme, at a temperature in the range of 20° C. to 100° C. for a time in the range of 5 minutes to 72 hours to create a hydrolyzed product from the biomass in the feedstock
    wherein the process is conducted without adding inorganic acid.

2. The process of claim 1, wherein the ratio of the weight of the solvent contacted with the feedstock to the weight of the feedstock is in the range of 40:60 to 90:10.

3. The process of claim 2, wherein the ratio of the weight of the solvent contacted with the feedstock to the weight of the feedstock is greater than 0.8:1.

4. The process of claim 1, wherein the ratio of the weight of the cellulose plus hydrolysis products of cellulose in the solvent to the weight of the cellulose in the ligno-cellulosic feedstock is greater than the ratio of 1:1.

5. The process of claim 2, wherein at least a portion of the catalyst composition is contacted with the feedstock before contacting the feedstock with at least a portion of the solvent.

6. The process of claim 4, wherein at least a portion of the catalyst composition is contacted with the feedstock before contacting the feedstock with at least a portion of the solvent.

7. The process of claim 2, wherein at least a portion of the catalyst composition is contacted with the feedstock after contacting the feedstock with at least a portion of the solvent.

8. The process of claim 4, wherein at least a portion of the catalyst composition is contacted with the feedstock after contacting the feedstock with at least a portion of the solvent.

9. The process of claim 2, wherein at least a portion of the catalyst composition is contacted with the feedstock simultaneously with contacting the feedstock with at least a portion of the solvent.

10. The process of claim 4, wherein at least a portion of the catalyst composition is contacted with the feedstock simultaneously with contacting the feedstock with at least a portion of the solvent.

11. The process of claim 2, wherein the ratio of the biomass to water of the feedstock is greater than the ratio of 1:0.9.

* * * * *